United States Patent
Greep et al.

(10) Patent No.: US 9,375,253 B2
(45) Date of Patent: Jun. 28, 2016

(54) ELECTROSURGICAL INSTRUMENT

(71) Applicant: Megadyne Medical Products, Inc., Draper, UT (US)

(72) Inventors: Darcy W. Greep, Herriman, UT (US); Paul R. Borgmeier, Salt Lake City, UT (US); Chad S. Frampton, American Fork, UT (US)

(73) Assignee: Megadyne Medical Products, Inc., Draper, UT (US)

( * ) Notice: Subject to any disclaimer, the term of this patent is extended or adjusted under 35 U.S.C. 154(b) by 257 days.

(21) Appl. No.: 13/831,502

(22) Filed: Mar. 14, 2013

(65) Prior Publication Data
US 2014/0276763 A1  Sep. 18, 2014

(51) Int. Cl.
| | | |
|---|---|---|
| A61B 18/14 | (2006.01) | |
| A61C 1/14 | (2006.01) | |
| B25F 1/04 | (2006.01) | |
| A61B 18/00 | (2006.01) | |

(52) U.S. Cl.
CPC .............. *A61B 18/1402* (2013.01); *A61C 1/14* (2013.01); *B25F 1/04* (2013.01); *A61B 2018/0091* (2013.01); *A61B 2018/1412* (2013.01); *A61B 2218/008* (2013.01)

(58) Field of Classification Search
CPC .... A61C 17/141; A61C 17/147; A61C 17/10; A61C 17/12; A61C 17/225; A61C 17/34; A61C 19/004; A61B 2017/0042; A61B 2017/00424; A61B 2017/00455; A61B 2018/00916; A61B 2018/00601; B23B 45/00; B25F 1/02; B25F 1/04; B25G 1/102; F16P 3/18

See application file for complete search history.

(56) References Cited

U.S. PATENT DOCUMENTS

| | | | |
|---|---|---|---|
| 2,311,424 A | 2/1943 | Weller, Jr. | |
| 2,329,439 A | 9/1943 | Hanssen | |
| 2,426,214 A | 8/1947 | Hewes | |
| 2,530,962 A | 11/1950 | Hare | |
| 2,542,019 A | 2/1951 | Fischer | |
| 4,683,884 A | 8/1987 | Hatfield | |
| 4,919,129 A * | 4/1990 | Weber, Jr. .......... | A61B 18/1402 604/35 |
| 4,921,492 A | 5/1990 | Schultz et al. | |

(Continued)

FOREIGN PATENT DOCUMENTS

| | | |
|---|---|---|
| CA | 2107230 | 10/1992 |
| CA | 2111617 | 7/1994 |

(Continued)

OTHER PUBLICATIONS

U.S. Appl. No. 12/429,867, Feb. 3, 2012, Office Action.

(Continued)

*Primary Examiner* — Andrew Gilbert
(74) *Attorney, Agent, or Firm* — Workman Nydegger

(57) ABSTRACT

An electrosurgical instrument that reduces the amount of fatigue experienced by a physician performing electrosurgery includes a hand piece with a utility conduit connected to the hand piece. The utility conduit can include an electrical cable and a smoke/fluid evacuation hose. The location at which the utility conduit exits the hand piece is selectively adjustable to reduce the resistance to the movement of the electrosurgical instrument created by the weight of the utility conduit. An electrosurgical instrument may also include an extendable shaft that allows for selective adjustment of the reach of the operational capabilities of the instrument.

24 Claims, 7 Drawing Sheets

(56) References Cited

U.S. PATENT DOCUMENTS

| | | | |
|---|---|---|---|
| 5,066,294 A | 11/1991 | Cosmescu | |
| 5,088,997 A | 2/1992 | Delahuerga et al. | |
| 5,108,389 A | 4/1992 | Cosmescu | |
| 5,114,422 A | 5/1992 | Cosmescu | |
| 5,160,334 A | 11/1992 | Billings et al. | |
| 5,181,916 A | 1/1993 | Reynolds | |
| 5,192,267 A | 3/1993 | Shapira | |
| 5,195,959 A | 3/1993 | Smith | |
| 5,196,007 A | 3/1993 | Ellman et al. | |
| 5,199,944 A | 4/1993 | Cosmescu | |
| 5,217,457 A | 6/1993 | Delahuerga et al. | |
| 5,234,429 A * | 8/1993 | Goldhaber | A61B 18/1402 606/37 |
| 5,244,462 A | 9/1993 | Delahuerga et al. | |
| 5,302,354 A | 4/1994 | Watvedt et al. | |
| 5,304,763 A | 4/1994 | Ellman et al. | |
| 5,312,397 A | 5/1994 | Cosmescu | |
| 5,318,516 A | 6/1994 | Cosmescu | |
| 5,318,565 A * | 6/1994 | Kuriloff | A61B 18/1402 604/119 |
| 5,358,552 A | 10/1994 | Seibert et al. | |
| 5,423,779 A | 6/1995 | Yeh | |
| 5,431,650 A | 7/1995 | Cosmescu | |
| 5,451,223 A | 9/1995 | Ben-Simhon | |
| 5,458,586 A | 10/1995 | Adiletta | |
| 5,460,602 A | 10/1995 | Shapira | |
| 5,520,651 A | 5/1996 | Sutcu et al. | |
| D372,086 S | 7/1996 | Grasso et al. | |
| 5,575,789 A | 11/1996 | Bell et al. | |
| 5,609,573 A | 3/1997 | Sandock | |
| 5,613,966 A | 3/1997 | Makower et al. | |
| 5,626,568 A | 5/1997 | Yeh et al. | |
| 5,662,647 A | 9/1997 | Crow | |
| 5,674,219 A * | 10/1997 | Monson et al. | 606/45 |
| 5,693,044 A * | 12/1997 | Cosmescu | 606/42 |
| 5,797,901 A | 8/1998 | Cosmescu | |
| 5,830,214 A | 11/1998 | Flom | |
| 5,836,909 A | 11/1998 | Cosmescu | |
| 5,836,944 A | 11/1998 | Cosmescu | |
| 5,868,722 A | 2/1999 | Yeh et al. | |
| 5,874,052 A | 2/1999 | Holland | |
| 6,001,077 A | 12/1999 | Ellman et al. | |
| 6,045,596 A | 4/2000 | Holland, Jr. et al. | |
| 6,053,886 A | 4/2000 | Holland, Jr. et al. | |
| D426,883 S | 6/2000 | Berman et al. | |
| 6,099,525 A | 8/2000 | Cosmescu | |
| 6,110,259 A | 8/2000 | Schultz et al. | |
| 6,117,134 A | 9/2000 | Cunningham | |
| 6,142,995 A | 11/2000 | Cosmescu | |
| 6,146,353 A * | 11/2000 | Platt, Jr. | 604/22 |
| 6,149,648 A | 11/2000 | Cosmescu | |
| 6,231,571 B1 | 5/2001 | Ellman | |
| 6,293,945 B1 * | 9/2001 | Parins | A61B 18/1402 606/45 |
| 6,302,881 B1 | 10/2001 | Farin | |
| 6,306,135 B1 | 10/2001 | Ellman et al. | |
| 6,355,034 B2 * | 3/2002 | Cosmescu | 606/45 |
| 6,368,309 B1 | 4/2002 | Yeh | |
| 6,379,350 B1 | 4/2002 | Sharkey | |
| 6,391,027 B1 | 5/2002 | Farin | |
| 6,458,125 B1 | 10/2002 | Cosmescu | |
| 6,524,307 B1 | 2/2003 | Palmerton et al. | |
| 6,530,924 B1 | 3/2003 | Ellman | |
| 6,544,210 B1 | 4/2003 | Trudel et al. | |
| 6,576,033 B1 | 6/2003 | Booth | |
| 6,585,791 B1 | 7/2003 | Garito et al. | |
| 6,589,316 B1 | 7/2003 | Schultz et al. | |
| 6,602,249 B1 | 8/2003 | Stoddard et al. | |
| 6,635,034 B1 | 10/2003 | Cosmescu | |
| 6,663,610 B1 | 12/2003 | Thompson et al. | |
| 6,685,665 B2 | 2/2004 | Booth et al. | |
| 6,702,812 B2 | 3/2004 | Cosmescu | |
| 6,716,211 B2 | 4/2004 | Mulier | |
| 6,746,504 B2 | 6/2004 | Booth | |
| 6,749,608 B2 | 6/2004 | Garito et al. | |
| D493,350 S | 7/2004 | Reschuke | |
| 6,802,842 B2 | 10/2004 | Ellman | |
| 6,881,236 B2 | 4/2005 | Schultz et al. | |
| 6,942,650 B1 | 9/2005 | Schultz et al. | |
| 7,004,939 B2 | 2/2006 | Mackay | |
| 7,033,353 B2 | 4/2006 | Stoddard et al. | |
| 7,083,601 B1 | 8/2006 | Cosmescu | |
| 7,112,199 B2 | 9/2006 | Cosmescu | |
| 7,198,626 B2 | 4/2007 | Lee | |
| 7,207,977 B2 | 4/2007 | Thompson et al. | |
| 7,241,294 B2 | 7/2007 | Reschke | |
| 7,258,712 B2 | 8/2007 | Schultz et al. | |
| 7,261,711 B2 | 8/2007 | Mulier | |
| D555,803 S | 11/2007 | Garito et al. | |
| 7,294,116 B1 | 11/2007 | Ellman et al. | |
| 7,329,253 B2 * | 2/2008 | Brounstein et al. | 606/41 |
| 7,387,625 B2 | 6/2008 | Hovda | |
| 7,393,351 B2 | 7/2008 | Woloszko | |
| 7,419,488 B2 | 9/2008 | Ciarrocca | |
| 7,435,247 B2 | 10/2008 | Woloszko | |
| 7,491,200 B2 | 2/2009 | Underwood | |
| 7,494,473 B2 | 2/2009 | Eggers | |
| 7,597,731 B2 | 10/2009 | Palmerton et al. | |
| 7,717,890 B2 | 5/2010 | Drogue et al. | |
| 7,717,912 B2 | 5/2010 | Woloszko | |
| D616,986 S | 6/2010 | Biegen et al. | |
| 7,761,188 B2 | 7/2010 | Palmerton et al. | |
| 7,789,946 B2 | 9/2010 | Schultz et al. | |
| 7,824,398 B2 | 11/2010 | Woloszko | |
| 7,828,797 B2 | 11/2010 | Eggers | |
| 7,892,337 B2 | 2/2011 | Palmerton et al. | |
| 7,935,109 B2 | 5/2011 | Cosmescu | |
| 7,959,698 B2 | 6/2011 | Schultz et al. | |
| 7,988,689 B2 | 8/2011 | Woloszko | |
| 8,002,732 B2 | 8/2011 | Visconti | |
| 8,057,470 B2 * | 11/2011 | Lee et al. | 606/41 |
| 8,095,241 B2 | 1/2012 | Palmerton et al. | |
| 8,137,345 B2 | 3/2012 | McNall | |
| 8,147,577 B2 | 4/2012 | Palmerton et al. | |
| 8,187,272 B2 | 5/2012 | Sensenbrenner | |
| 8,235,982 B2 | 8/2012 | Ward | |
| 8,241,278 B2 | 8/2012 | Sartor | |
| 8,317,786 B2 | 11/2012 | Dahla | |
| 8,323,279 B2 | 12/2012 | Dahla | |
| 8,414,576 B2 | 4/2013 | Cosmescu | |
| 8,460,289 B2 | 6/2013 | Sartor | |
| 8,518,018 B2 | 8/2013 | Minskoff | |
| 2001/0018586 A1 | 8/2001 | Cosmescu | |
| 2001/0051804 A1 * | 12/2001 | Mulier et al. | 606/45 |
| 2002/0013582 A1 | 1/2002 | Mulier | |
| 2002/0049438 A1 | 4/2002 | Sharkey | |
| 2002/0058938 A1 | 5/2002 | Cosmescu | |
| 2002/0103485 A1 | 8/2002 | Melnyk | |
| 2003/0135208 A1 | 7/2003 | Luigi | |
| 2003/0181904 A1 | 9/2003 | Levine | |
| 2004/0049183 A1 | 3/2004 | Ellman | |
| 2004/0162553 A1 | 8/2004 | Peng | |
| 2005/0107782 A1 | 5/2005 | Reschke | |
| 2005/0113825 A1 | 5/2005 | Cosmescu | |
| 2005/0124986 A1 | 6/2005 | Brounstein | |
| 2006/0264928 A1 * | 11/2006 | Kornerup et al. | 606/45 |
| 2006/0276783 A1 | 12/2006 | Cosmescu | |
| 2007/0129722 A1 | 6/2007 | Cosmescu | |
| 2007/0249990 A1 | 10/2007 | Cosmescu | |
| 2007/0255272 A1 | 11/2007 | Ariola | |
| 2007/0265615 A1 | 11/2007 | Ben-Simhon | |
| 2008/0103431 A1 | 5/2008 | Brounstein | |
| 2009/0018539 A1 * | 1/2009 | Cosmescu | 606/41 |
| 2009/0062791 A1 * | 3/2009 | Lee et al. | 606/45 |
| 2009/0069802 A1 | 3/2009 | Garito | |
| 2010/0094200 A1 | 4/2010 | Dean et al. | |
| 2010/0094283 A1 | 4/2010 | Cosmescu | |
| 2010/0174283 A1 | 7/2010 | McNall | |
| 2010/0274242 A1 * | 10/2010 | Greep | 606/41 |
| 2011/0077645 A1 | 3/2011 | Lin | |
| 2011/0190768 A1 * | 8/2011 | Shvetsov et al. | 606/48 |
| 2012/0101497 A1 | 4/2012 | Jayaraj | |
| 2012/0143186 A1 | 6/2012 | McNall | |
| 2012/0180664 A1 | 7/2012 | Lundquist | |

(56) References Cited

U.S. PATENT DOCUMENTS

| | | |
|---|---|---|
| 2012/0197250 A1 | 8/2012 | Ward |
| 2012/0203223 A1 | 8/2012 | Terry |
| 2012/0283718 A1 | 11/2012 | Cosmescu |
| 2012/0283728 A1* | 11/2012 | Cosmescu .................. 606/46 |
| 2012/0286179 A1 | 11/2012 | Palmerton et al. |
| 2013/0006236 A1 | 1/2013 | Greep |
| 2013/0110108 A1 | 5/2013 | Davison |
| 2013/0204246 A1 | 8/2013 | Greep |
| 2014/0046321 A1 | 2/2014 | Zinnati |

FOREIGN PATENT DOCUMENTS

| | | |
|---|---|---|
| CA | 2241516 | 7/1997 |
| CA | 2200535 | 9/1997 |
| CA | 2311424 | 7/1999 |
| CA | 2542019 | 7/1999 |
| CA | 2329439 | 10/1999 |
| CA | 2351649 | 5/2000 |
| CA | 2707676 | 5/2000 |
| CA | 2352880 | 8/2000 |
| CA | 2426214 | 5/2002 |
| CA | 2462825 | 4/2003 |
| CA | 2530962 | 1/2005 |
| CA | 2123960 | 7/2005 |
| CA | 2557280 | 10/2005 |
| CA | 2541694 | 10/2006 |
| CA | 2613950 | 11/2007 |
| CA | 2604402 | 3/2008 |
| CA | 2639108 | 2/2009 |
| CA | 2009151831 | 5/2009 |
| EP | 0447121 | 9/1991 |
| EP | 0538641 | 4/1993 |
| EP | 1016383 | 7/2000 |
| EP | 1188415 | 3/2002 |
| EP | 1388324 | 2/2004 |
| EP | 1532928 | 5/2005 |
| EP | 1584342 | 10/2005 |
| EP | 1707146 | 10/2006 |
| EP | 1795139 | 6/2007 |
| EP | 1902682 | 3/2008 |
| EP | 1938767 | 7/2008 |
| EP | 2438876 | 4/2012 |
| ES | 2159778 | 10/1998 |
| ES | 2238776 | 9/2005 |
| IL | 136254 | 3/1998 |
| IL | 139085 | 11/2001 |
| IL | 125102 | 7/2003 |
| IL | 159929 | 6/2004 |
| WO | 9108797 | 12/1990 |
| WO | 9108797 | 6/1991 |
| WO | 9219168 | 11/1992 |
| WO | 9623448 | 1/1996 |
| WO | 9619151 | 6/1996 |
| WO | 9723167 | 7/1997 |
| WO | 9931954 | 7/1999 |
| WO | 9953833 | 10/1999 |
| WO | 0028908 | 5/2000 |
| WO | 0032296 | 6/2000 |
| WO | 0238033 | 5/2002 |
| WO | 02060314 | 8/2002 |
| WO | 03030714 | 4/2003 |
| WO | 2005007214 | 1/2005 |
| WO | 2005094710 | 1/2005 |
| WO | 2005028078 | 3/2005 |
| WO | 2005046498 | 5/2005 |
| WO | 2007005159 | 1/2007 |
| WO | 2007123565 | 11/2007 |
| WO | 2007123656 | 11/2007 |
| WO | 2008109014 | 9/2008 |
| WO | 2012/154699 | 5/2012 |
| WO | 2012155922 | 11/2012 |

OTHER PUBLICATIONS

U.S. Appl. No. 12/429,867, Mar. 6, 2012, Notice of Allowance.
International Search Report and Written Opinion PCT/US 14/28080 dated Sep. 11, 2014.

* cited by examiner

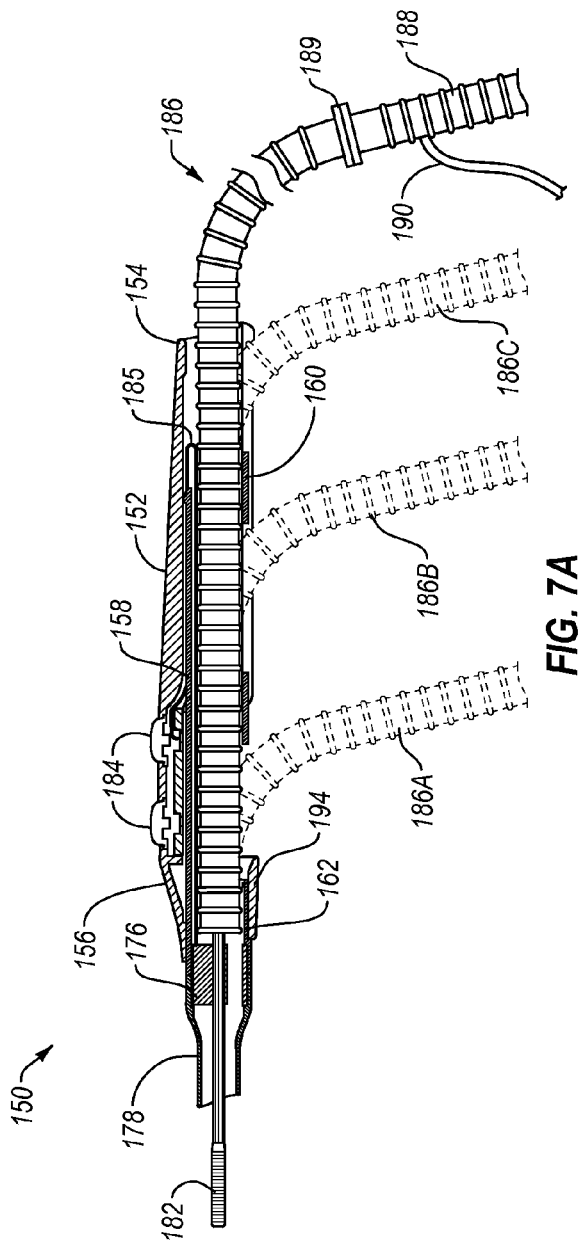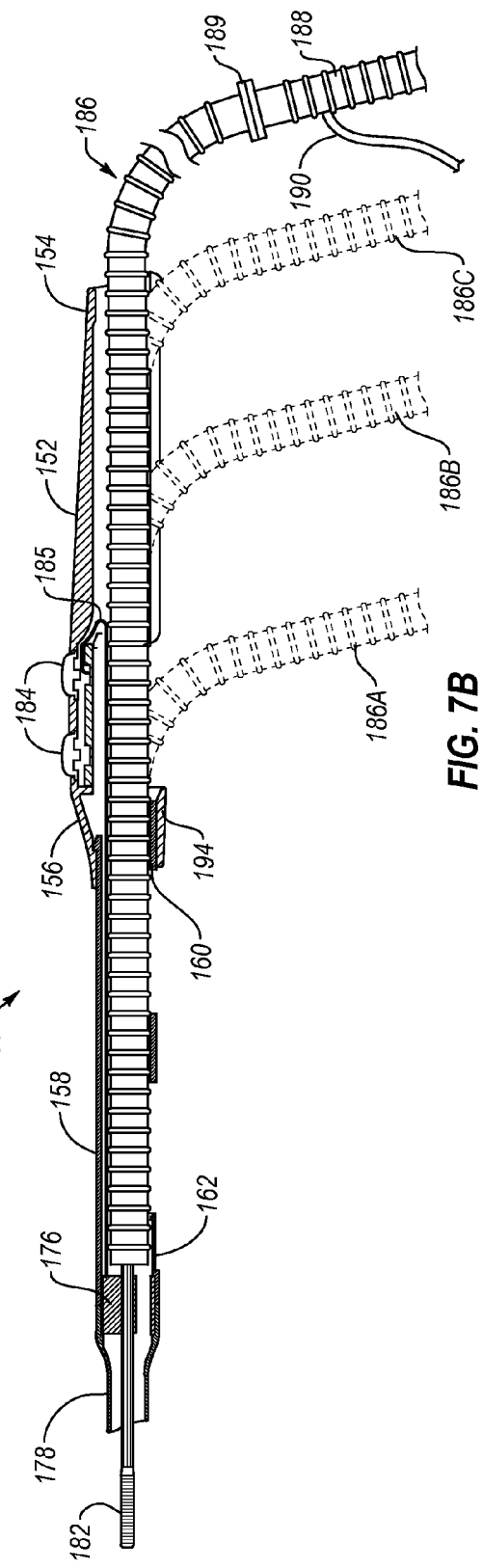
FIG. 7A
FIG. 7B

ELECTROSURGICAL INSTRUMENT

BACKGROUND

1. Technical Field

This invention relates to electrosurgical instruments. More particularly, the invention relates to electrosurgical instruments that facilitate the performance of various procedures or reduce the amount of fatigue experienced by users performing the procedures.

2. The Relevant Technology

As is known to those skilled in the art, modern surgical techniques typically employ radio frequency (RF) power to cut tissue and coagulate bleeding encountered in performing surgical procedures. For a historical perspective and details of such techniques, reference is made to U.S. Pat. No. 4,936,842, issued to D'Amelio et al., and entitled "Electroprobe Apparatus," the disclosure of which is incorporated by this reference.

As is known to those skilled in the medical arts, electrosurgery is widely used and offers many advantages including the use of a single surgical instrument for both cutting and coagulation. A monopolar electrosurgical generator system has an active electrode, such as in the form of an electrosurgical instrument having a hand piece and a conductive electrode or tip, which is applied by the surgeon to the patient at the surgical site to perform surgery and a return electrode to connect the patient back to the generator.

The electrode or tip of the electrosurgical instrument is small at the point of contact with the patient to produce an RF current with a high current density in order to produce a surgical effect of cutting or coagulating tissue. The return electrode carries the same RF current provided to the electrode or tip of the electrosurgical instrument, thus providing a path back to the electrosurgical generator.

To make the electrical connection for the RF current between the electrosurgical generator and the electrosurgical instrument, a cable having an electrically conductive core extends from the electrosurgical generator to the electrosurgical instrument. The cable may also include a cord with additional conductors. The cord provides a connection for transmitting control signals from the electrosurgical instrument to the electrosurgical generator. The control signals may be used to cause the generator to deliver RF currents to the electrosurgical instrument for different cutting modes such as cut, coagulate, and cut-coagulate blend.

When an electrosurgical instrument is used for cutting or coagulation, smoke is commonly produced. A surgeon or assistant uses a separate smoke evacuation device to remove the smoke from the surgical field. Smoke evacuation devices commonly include a suction wand connected to a vacuum device via tubing. The surgeon or assistant holds the suction wand close to the surgical site and the smoke is drawn into the suction wand and through the tubing. However, using a smoke evacuation device separate from the electrosurgical instrument is not ideal. Using a separate smoke evacuation device requires additional hands and instruments near the surgical site, which can obscure the surgeon's view of the surgical site and reduce the room available around the surgical site for the surgeon to move.

As a result, combination electrosurgical instrument and smoke evacuation devices have been developed. These combination devices often include a hand piece that can receive an electrode or tip in a distal end thereof for performing electrosurgical procedures. The hand piece is connected to a generator via a power cable to convey RF current to the electrode or tip. Additionally, a smoke evacuation hose is connected between the hand piece and a vacuum to draw smoke away from the surgical site. In some cases, the power cable runs through a portion of the smoke evacuation hose.

The power cables and smoke evacuation hoses have certain flexibility and weight characteristics that limit the ability of the physician during a surgical procedure. For example, the weight/moment-arm effect and drag of the power cable and/or the smoke evacuation hose as well as the connection location(s) of the power cable and/or smoke evacuation hose to the electrosurgical instrument limit the physician's ability to continually hold and use the electrosurgical instrument. The electrode or tip is received within one end (distal end) of the hand piece (commonly referred to as a pencil) and the power cable and/or smoke evacuation hose typically enter into the opposite end (proximal end) of the hand piece. As the physician manipulates the electrosurgical instrument during a surgical procedure, the weight of the power cable and/or smoke evacuation hose continually pulls on the proximal end of the hand piece. More specifically, as the physician moves his or her wrist or adjusts the orientation of the electrosurgical instrument with his or her fingers so as to bring the electrode into contact with the patient's tissue, the weight of the power cable and/or smoke evacuation hose resists the physician's movement. The constant resistance or drag created by the power cable and/or smoke evacuation hose can cause the physician to become fatigued during a surgical procedure that requires extensive and continual use of the electrosurgical instrument.

Additionally, many electrosurgical procedures are performed on very sensitive parts of the body, such as on or around the eyes. When performing such procedures, the physician must control the movements of the electrode with great precision and accuracy. The resistance or drag created by the power cable and/or smoke evacuation hose can make it more difficult for the physician to be as precise and accurate. For instance, when moving the electrosurgical instrument to make a delicate incision, the physician must accurately compensate for the resistance from the power cable and/or smoke evacuation hose. If the physician overcompensates, an incision that is too deep or too long can result. Alternatively, if the physician undercompensates, multiple passes may be required to achieve the desired incision. Furthermore, the fatigue caused by the resistance from the power cable and/or smoke evacuation hose can adversely affect the physician's ability to accurately compensate for the resistance from the power cable and/or smoke evacuation hose.

Furthermore, some existing combination electrosurgical instrument and smoke evacuation devices include an extendable portion, typically in the form of an enclosed tube, which can be selectively extended from the distal end of the hand piece. When the extendable portion is extended, the device is able to reach deeper into a surgical site to evacuate smoke. The extendable portion is typically slidably disposed within an internal chamber in the hand piece. A seal is used between the extendable portion and the internal chamber to prevent smoke from escaping the hand piece at the distal end. Similarly, a seal is used at the proximal end of the hand piece, where the smoke evacuation hose is connected to the internal chamber, to prevent smoke from escaping from the hand piece at the proximal end. Thus, the internal channel acts as part of a flow conduit through which the smoke is evacuated.

Combination electrosurgical instrument and smoke evacuation devices that utilize the foregoing internal chamber design have a number of drawbacks. For instance, this arrangement usually increases the complexity of the hand piece design, assembly, and physical size. By way of example, seals must be properly disposed in both the proximal and distal ends of the hand piece in order to seal off the internal chamber and maintain the vacuum pressure therein. Additionally, the ergonomics of the hand piece are also hindered because the hand piece must remain linear to accommodate the extending portion. Still further, the smoke evacuation hose must be connected at the proximal end of the hand piece, which leads to the aforementioned undesirable resistance and moment arm effects.

The subject matter claimed herein is not limited to embodiments that solve any disadvantages or that operate only in environments such as those described above. Rather, this background is only provided to illustrate one exemplary technology area where some embodiments described herein may be practiced.

BRIEF DESCRIPTION OF THE DRAWINGS

To further clarify the above and other advantages and features of the present invention, a more particular description of the invention will be rendered by reference to specific embodiments thereof which are illustrated in the appended drawings. It is appreciated that these drawings depict only illustrated embodiments of the invention and are therefore not to be considered limiting of its scope. The invention will be described and explained with additional specificity and detail through the use of the accompanying drawings in which:

FIG. 7A is a cross-sectional view of the electrosurgical instrument of FIG. 3 with an extendable shaft in a fully retracted position;

FIG. 7B is a cross-sectional view of the electrosurgical instrument of FIG. 3 with the extendable shaft in a fully extended position;

DETAILED DESCRIPTION

The present invention relates to hand-held instruments or hand pieces that facilitate the performance of various procedures while reducing the amount of fatigue experienced by users performing the procedures. In some embodiments a hand-held instrument or hand piece is an electrosurgical instrument that holds an electrode tip in one end thereof. The hand piece is connected to a utility conduit. In embodiments that include an electrode tip, the utility conduit may include an electrical cable that is connected to an electrosurgical generator. The utility conduit may also or alternatively include a smoke/fluid evacuation hose that is connected to a vacuum device. Further, the utility conduit may include other tubes, cables, or the like for conveying electrical signals, smoke, fluid, and the like to or from the electrosurgical instrument. Still further, the hand piece may include an extendable shaft that increases the reach of the operational capabilities (e.g., electrical current delivery, smoke capture, etc.) of the device.

In contrast to most electrosurgical instruments that have an electrical cable and/or a smoke/fluid evacuation hose connected to a proximal end of the hand piece, the electrosurgical instrument of the present invention provides for the utility conduit to be connected to the hand piece at a distal end of the hand piece. Connecting the utility conduit to the distal end of the hand piece reduces the resistance to the movement of the electrosurgical instrument created by the weight/moment-arm effect and drag of the utility conduit. The reduced resistance leads to less fatigue in the physician's hand and arm during electrosurgery. In addition to connecting the utility conduit to the distal end of the hand piece, the hand piece can be configured to allow the physician to adjust the location at which the utility conduit exits the hand piece. The physician can, therefore, selectively adjust the utility conduit relative to the hand piece in order to customize the electrosurgical instrument to the physician's liking.

Figure 1:
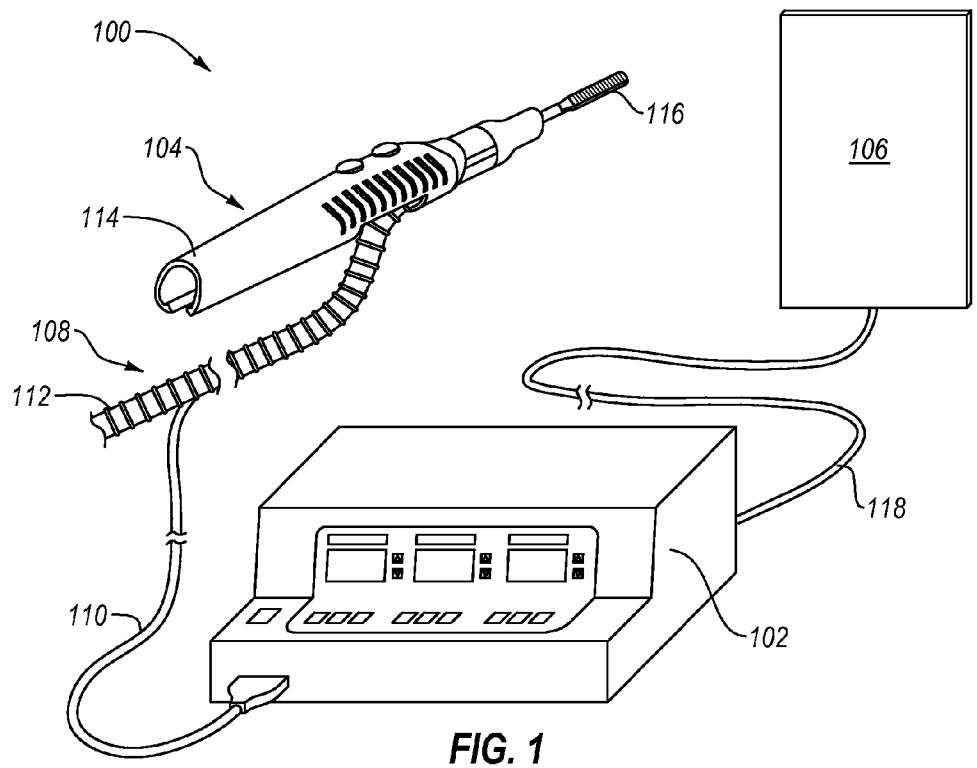
FIG. 1 illustrates an electrosurgical system with an electrosurgical instrument according to one exemplary embodiment of the present invention.

Referring to FIG. 1, an exemplary environment is illustrated that provides one operating environment for use of the present invention. In FIG. 1, an electrosurgical system 100 is illustrated, which includes a signal generator 102, an electrosurgical instrument 104, and a return electrode 106. Generator 102, in one embodiment, is an RF wave generator that produces RF electrical energy. Connected to electrosurgical instrument 104 is a utility conduit 108. In the illustrated embodiment, utility conduit 108 includes a cable 110 that communicates the RF electrical energy from generator 102 to electrosurgical instrument 104. As also illustrated, the present embodiment of utility conduit 108 also includes an evacuation hose 112 that conveys smoke and/or fluid away from a surgical site.

Generally, electrosurgical instrument 104 includes a hand piece or pencil 114 and an electrode tip 116. Electrosurgical instrument 104 communicates the RF electrical energy to a patient to cut tissue and/or cauterize blood vessels of the patient's body. Specifically, an electrical discharge is delivered from electrode tip 116 to the patient in order to cause heating of cellular matter of the patient that is in close contact with electrode tip 116. The heating takes place at an appropriately high temperature to allow electrosurgical instrument 104 to be used to perform electrosurgery. Return electrode 106 and a cable 118 provide a return electrical path to generator 102 for any excess charge that dissipates into surrounding tissue of the patient's body.

Figure 2:
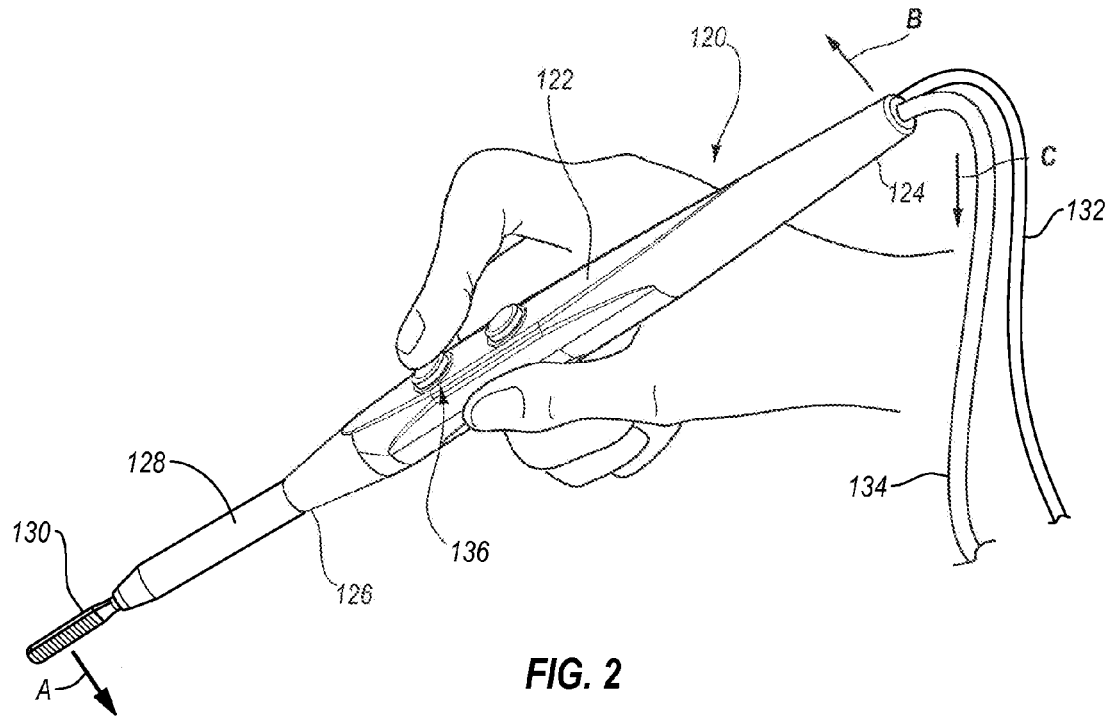
FIG. 2 illustrates one manner of holding an electrosurgical instrument.

Illustrated in FIG. 2 is an electrosurgical instrument 120 commonly used to perform electrosurgical procedures and evacuate smoke from a surgical site. Electrosurgical instrument 120 includes a hand piece 122 having a proximal end 124 and a distal end 126. An extendable evacuation tube 128 is selectively extendable from distal end 126 and includes a channel extending therethrough. An electrode tip 130 is received within the distal end of the evacuation tube 128. A power cable 132 and an evacuation hose 134 are connected to electrosurgical instrument 120 at proximal end 124. Cable 132 communicates electrical energy from an electrosurgical generator to electrosurgical instrument 120. The electrical energy is passed through electrode tip 130 and into a patient's tissue.

Smoke resulting from the electrosurgical procedure is drawn into evacuation tube 128, through an internal chamber in hand piece 122, and through evacuation hose 134. A sufficient vacuum pressure must be maintained within hand piece 122 in order to effectively evacuate smoke from the surgical site. Accordingly, the internal chamber inside hand piece 122 is a closed chamber and is sealed off at each end. More specifically, the interface between the internal chamber inside hand piece 122 and evacuation tube 128 is sealed. Similarly, the connection between evacuation hose 134 and the internal chamber is also sealed.

Electrosurgical instruments, such as electrosurgical instrument 120, are commonly referred to as electrosurgical pencils or pens because in use they are often held in the same manner that a pencil or pen is held when writing. FIG. 2 illustrates one of the most common manners by which physicians hold electrosurgical instruments during an electrosurgical procedure. As can be seen, hand piece 122 is laid through the crook of the hand and is held in place by the middle finger and thumb. The index finger is placed on top of hand piece 122 to further hold hand piece 122 in place as well as to activate input device 136.

As noted elsewhere herein, the flexibility, weight/moment-arm, and drag characteristics of cable 132 and evacuation hose 134 and the connection locations of cable 130 and evacuation hose 134 to hand piece 122 limit the ability of the physician during a surgical procedure. While holding electrosurgical instrument 120 as shown in FIG. 2, a physician will perform electrosurgery by activating input device 136 and moving electrode tip 130 into contact with the patient's tissue. To make contact between electrode tip 130 and the patient's tissue, the physician will move his or her wrist or fingers to adjust the position and/or orientation of electrosurgical instrument 120.

For instance, the physician may move his or her wrist or finders so that electrode tip 130 moves in the direction of arrow A toward the patient's tissue. Notably, as the physician moves electrode tip 130 in the direction of arrow A, proximal end 124 moves in the direction of arrow B. The weight of cable 132 and evacuation hose 134 constantly pulls proximal end 124 in the direction of arrow C. Thus, the weight of cable 132 and evacuation hose 134 resists the movement of proximal end 124 in the direction of arrow B.

The resistance created by the weight of cable 132 and evacuation hose 134 is accentuated by the location at which cable 132 and evacuation hose 134 are connected to hand piece 122. As is understood, a torque is created by applying a force at a distance from a pivot point. The magnitude of the torque is a result of the magnitude of the applied force and the distance between the pivot point and the location where the force is applied. In the case of electrosurgical instrument 120, the weight of cable 132 and evacuation hose 134 is the force that contributes to the generation of the resistive torque. Additionally, the location at which cable 132 and evacuation hose 134 attach to hand piece 122 and how hand piece 122 is held creates the lever arm through which the weight of cable 132 and evacuation hose 134 works to create the torque. More specifically, cable 132 and evacuation hose 134 enter or are connected to hand piece 122 at or near proximal end 124. When electrosurgical instrument 120 is held as shown in FIG. 2, proximal end 124 is positioned above and away from the crook of the physician's hand, which acts as the pivot point. The weight of cable 132 and evacuation hose 134 pulls down on proximal end 124, thereby creating a torque or moment-arm. Because the magnitude of the torque is dependent on the distance between the pivot point and the force, the greater the distance is between the crook of the hand and the connection point (i.e., between hand piece 122 and the ends of cable 132 and evacuation hose 134), the greater the torque will be. Understandably, the larger the torque is, the greater amount of resistance the physician will experience when manipulating electrosurgical instrument 120.

To overcome the resistance created by the weight of cable 132 and evacuation hose 134, the physician must exert additional energy to move electrosurgical instrument 120 into the desired orientation. Continuously working against the resistance created by cable 132 and evacuation hose 134 can cause the physician's hand, wrist, and/or arm to become fatigued during an electrosurgical procedure. This fatigue can also lead to a loss of accuracy and precision in the performance of the procedure.

Attention is now directed to FIGS. 3-12, which illustrate hand pieces according exemplary embodiments of the present invention. More specifically, the illustrated hand pieces are electrosurgical instruments that reduce the resistance created by electrical cables and/or evacuation hoses, and/or provide increased reach for operational capabilities (e.g., electrical current delivery, smoke/fluid evacuation, etc.). The embodiments shown in FIGS. 3-12 include an extendable shaft that is selectively extendable from the hand piece to increase the reach of the electrical current delivery and/or smoke/fluid evacuation capabilities. The term "extendable shaft" is used herein to broadly refer to any structure capable of performing the functions described herein in connection with an extendable shaft. Thus, an extendable shaft may include one or more extendable rods, rails, channels, or the like. Additionally, the extendable shaft may be solid, hollow, or have various cross-sectional shapes (e.g., U- or C-shaped cross-section). Furthermore, the distal end of the extendable shaft may include an electrode tip mounted therein for delivery of electrical current to patient tissue. The distal end of the extendable shaft may also include a nozzle into which the smoke and/or fluid is drawn.

As also shown in the Figures, a utility conduit is connected near the distal end of the extendable shaft. A power cable of the utility conduit delivers electrical current to the electrode tip while an evacuation hose of the utility conduit is in fluid communication with the nozzle to convey away the smoke and/or fluid. In addition to the utility conduit being connected near the distal end of the extendable shaft, the utility conduit can also exit the electrosurgical instruments from various locations along the length of the hand piece, referred to hereinafter as the "exit locations." Allowing a user to select and adjust the exit location of the utility conduit enables the user to customize the electrosurgical instrument to his or her liking, such as to reduce or eliminate the resistance created by the weight of the utility conduit, which can reduce the fatigue experienced during an electrosurgical procedure.

For example, FIGS. 3-9 illustrate one exemplary embodiment of an electrosurgical instrument 150 according to the present invention. Electrosurgical instrument 150 includes a hand piece 152 having a proximal end 154 and a distal end 156. An extendable shaft 158 is movably disposed within hand piece 152. Extendable shaft 158 is usable to increase the reach of electrosurgical instrument 150 to perform electrosurgical procedures and/or evacuate smoke/fluid from a surgical site.

Figure 3:
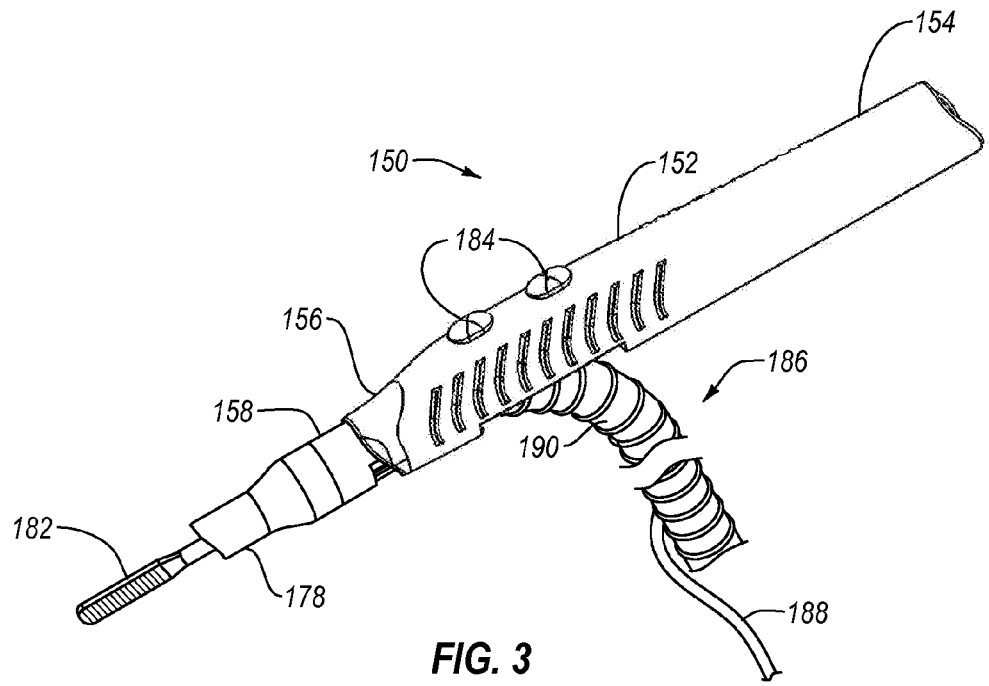
FIG. 3 is a perspective view of an electrosurgical instrument according to an exemplary embodiment of the present invention.
Figure 4:
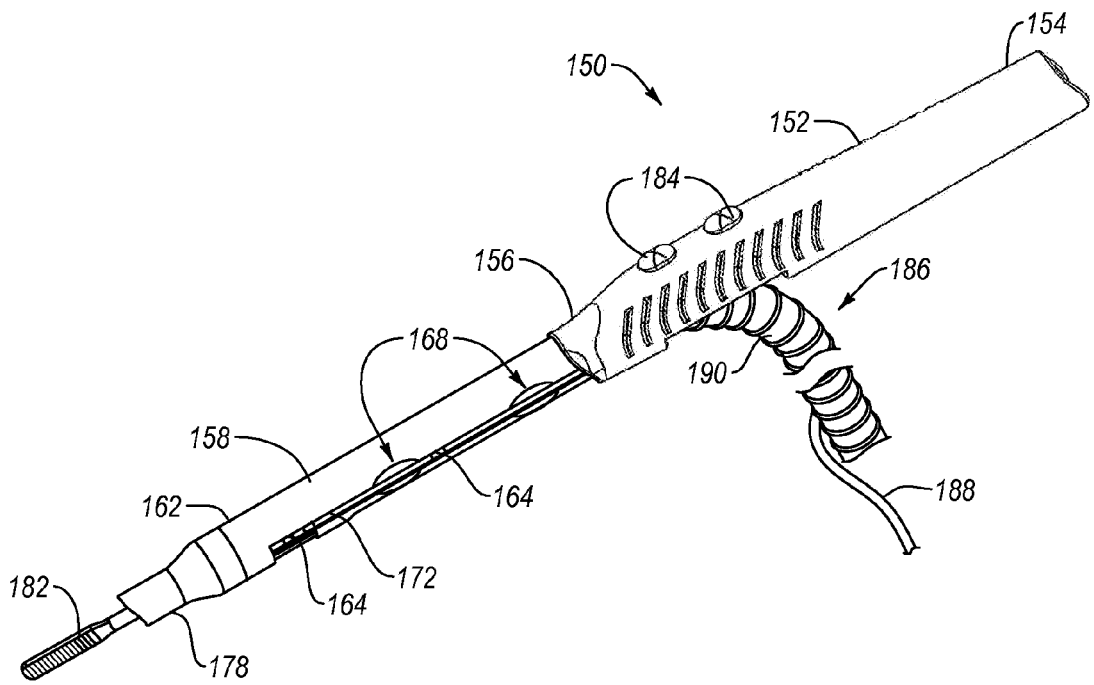
FIG. 4 is another perspective view of the electrosurgical instrument of FIG. 3 in an extended configuration.

Extendable shaft 158 is movable relative to hand piece 152 between a fully retracted position and a fully extended position. The fully retracted position of extendable shaft 158 is shown in FIG. 3 and the fully extended position is shown in FIG. 4. According to the illustrated embodiment, most of extendable shaft 158 is disposed inside of hand piece 152 when extendable shaft 158 is in the fully retracted position. Nevertheless, as can be seen in FIG. 3, at least a portion of extendable shaft 158 extends out of distal end 156 and is disposed outside of hand piece 152 when extendable shaft 158 is in the fully retracted position. In other embodiments, however, extendable shaft 158 is disposed entirely within hand piece 152 when extendable shaft 158 is in the fully retracted position.

Extendable shaft 158 is selectively movable from the fully retracted position shown in FIG. 3 to the fully extended position shown in FIG. 4. In the illustrated embodiment, extendable shaft 158 is slidable relative to hand piece 152 such that extendable shaft 158 can be selectively slid between the fully retracted and fully extended positions.

In some embodiments, including the illustrated embodiment, extendable shaft 158 is also movable between one or more intermediate positions. In the one or more intermediate positions, extendable shaft 158 extends out of hand piece 152 further than when extendable shaft 158 is in the fully retracted position, but not as far as when extendable shaft 158 is in the fully extended position.

Figure 8:
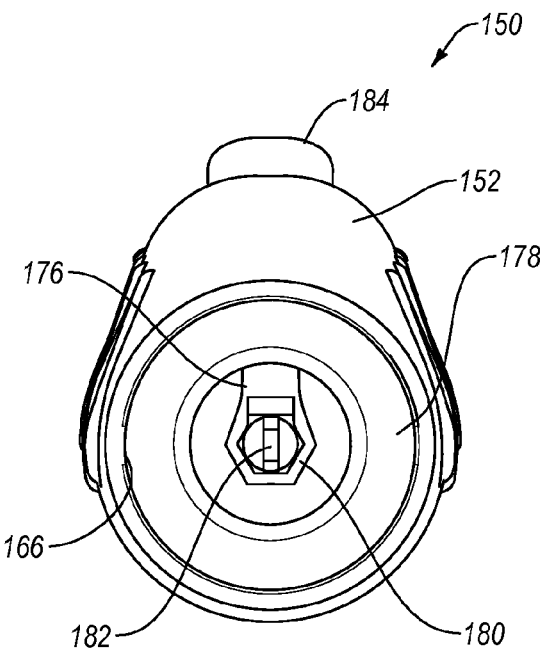
FIG. 8 is an end view of a distal end of the electrosurgical instrument of FIG. 3.

In the illustrated embodiment, extendable shaft 158 is selectively securable in each of the fully retracted, the fully extended, and the one or more intermediate positions. Extendable shaft 158 includes a proximal end 160 (FIGS. 6-7B) and a distal end 162. Disposed along the length of extendable shaft 158 between proximal and distal ends 160, 162 are a plurality of recesses 164 (FIG. 4). Disposed on an interior surface of hand piece 152 near distal end 156 are one or more protrusions 166 (FIG. 8). Recesses 164 and the one or more protrusions 166 cooperate to selectively secure extendable shaft 158 in each of the fully retracted, the fully extended, and the one or more intermediate positions.

For instance, when extendable shaft 158 is in the fully retracted position shown in FIG. 3, the one or more protrusions 166 may extend into one or more recesses 164 disposed adjacent to distal end 162 of extendable shaft 158, thereby securing extendable shaft 158 in the fully retracted position. Similarly, when extendable shaft 158 is in the fully extended position shown in FIG. 4, the one or more protrusions 166 may extend into one or more recesses 164 disposed adjacent to proximal end 160 of extendable shaft 158, thereby securing extendable shaft 158 in the fully extended position. Likewise, when extendable shaft 158 is in one of the one or more intermediate positions, the one or more protrusions 166 may extend into one or more recesses 164 disposed between proximal and distal ends 160, 162 of extendable shaft 158, thereby securing extendable shaft 158 in one of the one or more intermediate positions.

It is understood that the illustrated recesses and protrusions are merely exemplary. In other embodiments, for instance, an extendable shaft may have a plurality of protrusions disposed along the length thereof and one or more recesses may be formed on an interior surface of a hand piece. As with the illustrated embodiment, such recesses and protrusions may cooperate to selectively secure the extendable shaft in various discrete positions (e.g., fully retracted, fully extended, one or more intermediate positions) relative to the hand piece.

Figure 6:
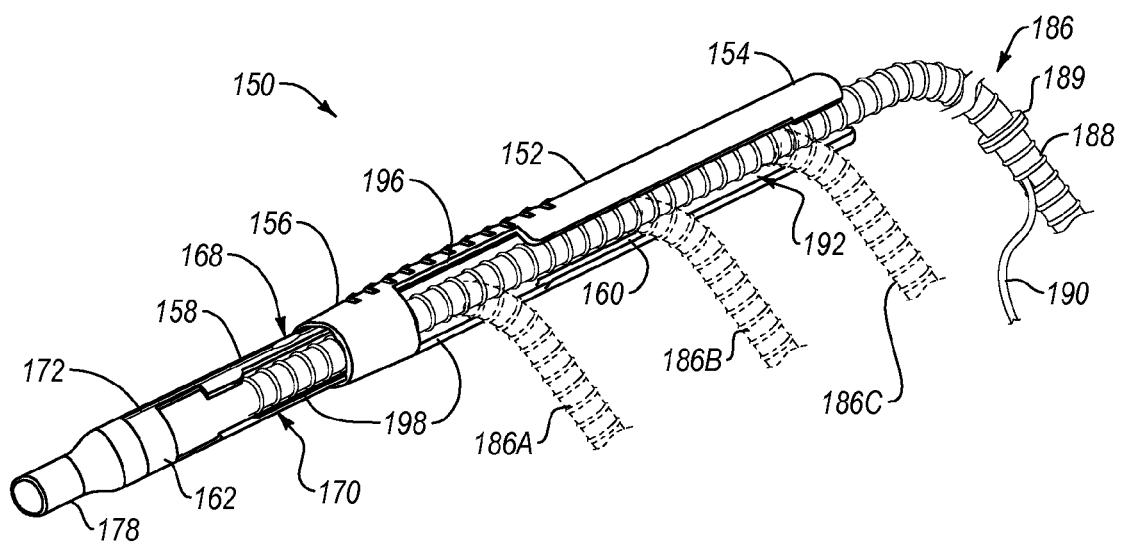
FIG. 6 is a bottom perspective view of the electrosurgical instrument of FIG. 3 showing slots formed therein.

The recesses 164 and protrusions 166 may be selectively disengaged from one other to enable extendable shaft 158 to be moved between the fully retracted, the fully extended, and the one or more intermediate positions. For instance, extendable shaft 158 may be compressed adjacent to distal end 156 to disengage protrusions 166 from recesses 164. As shown in FIGS. 4 and 6, for instance, extendable shaft 158 may optionally include depression areas 168 where extendable shaft 158 may be compressed to disengage protrusions 166 from recesses 164. Depression areas 168 may provide a visual and/or tactile indication to a user as to where extendable shaft 158 may be compressed in order to disengage protrusions 166 from recesses 164.

Figure 5:
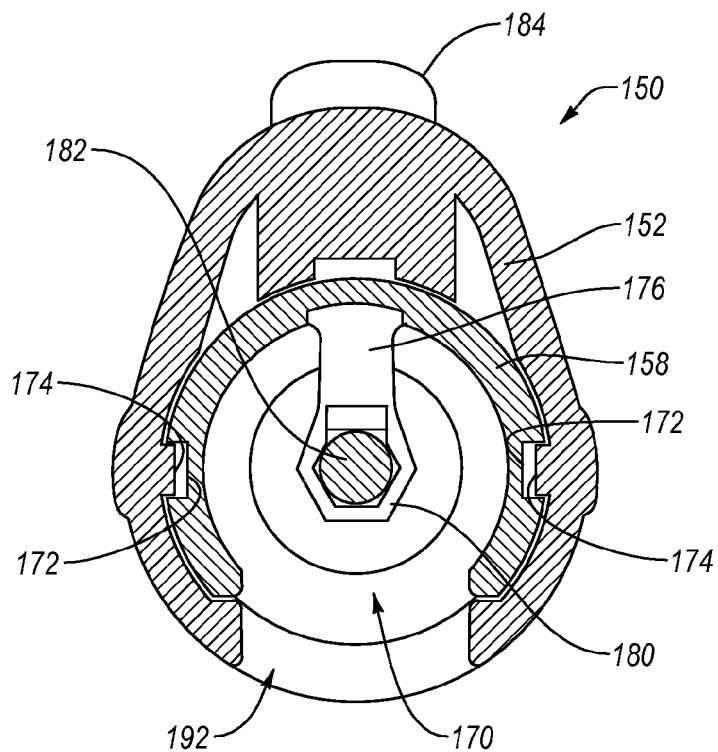
FIG. 5 is a cross-sectional view of a proximal end of the electrosurgical instrument of FIG. 3.

To facilitate the compression of extendable shaft 158, a slot 170 is formed therein, as can be seen in FIGS. 5 and 6. Slot 170 extends along the length of extendable shaft 158 from proximal end 160 toward distal end 162. Slot 170 enables the sides of extendable shaft 158 to be compressed closer together, which enables protrusions 166 to be disengaged from recesses 164. Thus, a user may selectively adjust how far extendable shaft 158 extends from hand piece 152 by first compressing the sides of extendable shaft 158 (e.g., at the depression areas 168 adjacent to distal end 156 of hand piece 152) to disengage protrusions 166 from recesses 164. With protrusions 166 disengaged from recesses 164, the user may slide extendable shaft 158 relative to hand piece 152 so that extendable shaft 158 is positioned in the fully retracted, the fully extended, or one of the one or more intermediate positions. When extendable shaft 158 is in the desired position, protrusions 166 may engage recesses 164 to secure extendable shaft 158 in the desired position.

In the illustrated embodiment as shown in FIG. 5, hand piece 152 has a generally circular interior surface and extendable shaft 158 has a generally circular exterior surface. Such corresponding surfaces may allow for relative rotational movement between hand piece 152 and extendable shaft 158. While this may be desirable in some instances, it may be less desirable in other instances. Accordingly, hand piece 152 and extendable shaft 158 may include cooperating features to prevent relative rotation therebetween during use or when extendable shaft 158 is being repositioned between the retracted, extended, and intermediate positions.

For instance, as shown in FIGS. 4 and 5, extendable shaft 158 includes one or more tracks 172 and hand piece 152 includes one or more rails 174. Tracks 172 may take the form of one or more grooves formed in an exterior surface of extendable shaft 158. Tracks 172 may extend along at least a portion of the length of extendable shaft 158. Rails 174 are formed or otherwise disposed on an interior surface of hand piece 152. Tracks 172 receive rails 174 therein. Tracks 172 and rails 174 cooperate to enable extendable shaft 158 to slide longitudinally relative to hand piece 152 while also preventing hand piece 152 and extendable shaft 158 from rotating relative to one another. In other embodiments, a hand piece and an extendable shaft may include non-circular interfacing surfaces that prevent relative rotational movement therebetween.

Connected to distal end 162 of extendable shaft 158 is a collet 176 and a nozzle 178. As shown in FIGS. 7A and 7B, for example, collet 176 is mounted partially within distal end 162 of extendable shaft 158 and nozzle 178 is mounted on collet 176. As best seen in FIGS. 5 and 8, collet 176 includes a mount 180 for receiving the shaft of an electrode tip 182 therein. Collet 176 is configured to deliver electrical current to electrode tip 182 upon activation of one of input devices 184 on hand piece 152.

As shown in FIGS. 7A and 7B, input devices 184 are in electrical communication with collet 176 by way of a flexible electrical ribbon 185. When one of input devices 184 is activated, a signal is sent via electrical ribbon 185 that allows electrical current to flow through collet 176 and into electrode tip 182. When electrode tip 182 is in close proximity to patient tissue, the electrical current is transferred to the patient tissue to perform an electrosurgical procedure. In contrast, when input devices 184 are not activated, electrical current does not flow to electrode tip 182, thereby preventing the performance of an electrosurgical procedure.

In the illustrated embodiment, electrical ribbon 185 is connected between input devices 184 and collet 176. As seen in FIGS. 7A and 7B, a first portion of electrical ribbon 185 is disposed between hand piece 152 and extendable shaft 158, and a second portion of electrical ribbon 185 is disposed inside of extendable shaft 158. The first portion of electrical ribbon 185 extends from input devices 184 towards proximal end 154 of hand piece 152. After extending proximally past proximal end 160 of extendable shaft 158, electrical ribbon 185 extends around proximal end 160 and inside extendable shaft 158. The second portion of electrical ribbon 185 then extends distally toward collet 176.

The electrical current used to perform electrosurgical procedures is delivered to hand piece 152 by way of a utility conduit 186. In the illustrated embodiment, utility conduit 186 includes a power cable 188 and an evacuation hose 190. Power cable 188 delivers the electrical current used to perform electrosurgical procedures from a signal generator (e.g., signal generator 102, FIG. 1) to hand piece 152. Power cable 188 may be connected to input devices 184, electrical ribbon 185, collet 176, or combinations thereof.

The performance of electrosurgical procedures often results in the creation of smoke at the surgical site. The smoke can be removed from the surgical site by way of electrosurgical instrument 150. More specifically, the smoke may be drawn into nozzle 178 and conveyed away via evacuation hose 190. In the illustrated embodiment, one end of evacuation hose 190 is connected to distal end 162 of extendable shaft 158 and is in fluid communication with nozzle 178. A second end of evacuation hose 190 may be connected to a vacuum device that draws the smoke (or other fluids) into nozzle 178, through evacuation hose 190, and away from the surgical site. Power cable 188 or another cable may connect hand piece 152 to the vacuum device so that hand piece 152 may control the operation of the vacuum device.

The connection between utility conduit 186 and distal end 162 may allow for relative movement between electrosurgical instrument 150 and utility conduit 186. For instance, a swivel may be connected between distal end 162 and utility conduit 186. The swivel may allow for electrosurgical instrument 150 to rotate relative to utility conduit 186 or vice versa. Such relative movement may reduce or eliminate longitudinal rotational torque of electrosurgical instrument 150 by utility conduit 186.

In addition or as an alternative to electrosurgical instrument 150 and utility conduit 186 being movably connected together (e.g., with a swivel), utility conduit 186 may include two or more sections that are connected together in a manner that allows for relative movement between adjacent sections. For instance, as shown in the FIG. 9, utility conduit 186 may include a first section 187A and a second section 187B that are connected together via a swivel 189. Swivel 189 may include a first half and a second half that are able to rotate relative to one another. First section 187A may be connected to the first half of swivel 189 and second section 187B may be connected to the second half of swivel 189. The ability of the first and second halves of swivel 189 to rotate relative to one another enables first and second sections 187A, 187B of utility conduit 186 to also rotate relative to one another. As a result, electrosurgical instrument 150 and first section 187A are able to move and rotate relative to second section 187B with less longitudinal rotational torque.

In the illustrated embodiment, power cable 188 is shown extending through the interior of evacuation hose 190 for a length thereof and exiting evacuation hose 190 proximal to hand piece 152. It is understood that this arrangement is merely exemplary. In other embodiments, for instance, power cable 190 may extend through the entire length of evacuation hose 190. Alternatively, power cable 190 may not extend through evacuation hose 190 at all. Additionally, although utility conduit 186 is described herein as including both power cable 188 and evacuation hose 190, such configuration is merely exemplary. In other embodiments, a utility conduit may only include a power cable. In still other embodiments, a utility conduit may only include an evacuation hose. In still other embodiments, a utility conduit may include one or more cables and/or one or more hoses.

According to the present embodiment, utility conduit 186 is connected to distal end 162 of extendable shaft 158. As a result, when extendable shaft 158 is moved between the fully retracted position and the fully extended position, utility conduit 186 moves through or relative to hand piece 152. For instance, when extendable shaft 158 is moved distally from the fully retracted position to the fully extended position or one of the intermediate positions, utility conduit 186 also moves distally through hand piece 152. Similarly, when extendable shaft 158 is moved proximally (e.g., from the fully extended position to the fully retracted position or one of the intermediate positions, or from one of the intermediate positions to the fully retracted position), utility conduit 186 also moves proximally through hand piece 152.

As shown in FIG. 7A, for instance, when extendable shaft 158 is in the fully retracted position, the distal end of utility conduit 186 is positioned adjacent to distal end 156 of hand piece 152. When extendable shaft 158 is moved distally to the fully extended position shown in FIG. 7B, utility conduit 186 is also moved distally so that the distal end of utility conduit 186 is spaced distally away from distal end 156 of hand piece 152.

As best seen in FIGS. 5 and 6, hand piece 152 includes a slot 192 that extends along the length of hand piece 152 from proximal end 154 to a retainer portion 194 at or near distal end 156. Slot 170 in extendable shaft 158 and slot 192 in hand piece 152 are aligned with one another. The alignment of slots 170, 192 enables utility conduit 186 to exit electrosurgical instrument 150 at various exit locations along the length of hand piece 152. That is, while utility conduit 186 is connected to distal end 162 of extendable shaft 158, a portion of utility conduit 186 can be positioned within extendable shaft 158 and hand piece 152 so that utility conduit 186 exits or extends from hand piece 152 at any one of a number of locations along the length of hand piece 152, whether adjacent to or distant from distal end 156 of hand piece 152.

Slots 170, 192 are sized to selectively receive and retain at least a portion of utility conduit 186 within hand piece 152 and extendable shaft 158. That is, slots 170, 192 are sized to snuggly retain utility conduit 186 within hand piece 152 and extendable shaft 158 so that utility conduit 186 does not inadvertently come out of slots 170, 192 while electrosurgical instrument 150 is being used. Nevertheless, slots 170, 192 are also sized to allow at least a portion of utility conduit 186 to be selectively removed from hand piece 152 and extendable shaft 158 therethrough.

As a result of the size and configuration of slot 192, hand piece 152 is substantially hollow between distal end 156 and proximal end 154. For instance, in some embodiments, hand piece 152 is at least 70% hollow. More specifically, in some embodiments, slot 192 reduces the overall volume of hand piece 152 by more than 70%. In the illustrated embodiment, for example, hand piece 152 has a width between opposing side surfaces of about 0.65 inches and slot 192 has a width of about 0.55 inches. Accordingly, the ratio between the widths of hand piece 152 and slot 192 is about 0.85, resulting in hand piece 152 being about 85% hollow. It will be appreciated, however, that the foregoing percentages and ratios are merely exemplary. By way of non-limiting example, a hand piece may be substantially hollow if the ratio between the width of the hand piece and the width of the longitudinal channel is greater than about 25%, about 40%, about 50%, or about 75%.

Slots 170, 192 allow a user to select the exit location of utility conduit 186 by positioning differing lengths of utility conduit 186 within hand piece 152 and extendable shaft 158. For instance, as shown in FIGS. 6, 7A, 7B, and 9, a user may position utility conduit 186 in hand piece 152 and extendable shaft 158 so that utility conduit 186 exits hand piece 152 through proximal end 154, similar to conventional electrosurgical and smoke evacuation instruments. Alternatively, less of utility conduit 186 may be positioned within hand piece 152 and extendable shaft 158 so that utility conduit 186 exits hand piece 152 and extendable shaft 158 through one or both of slots 170, 192.

Figure 9:
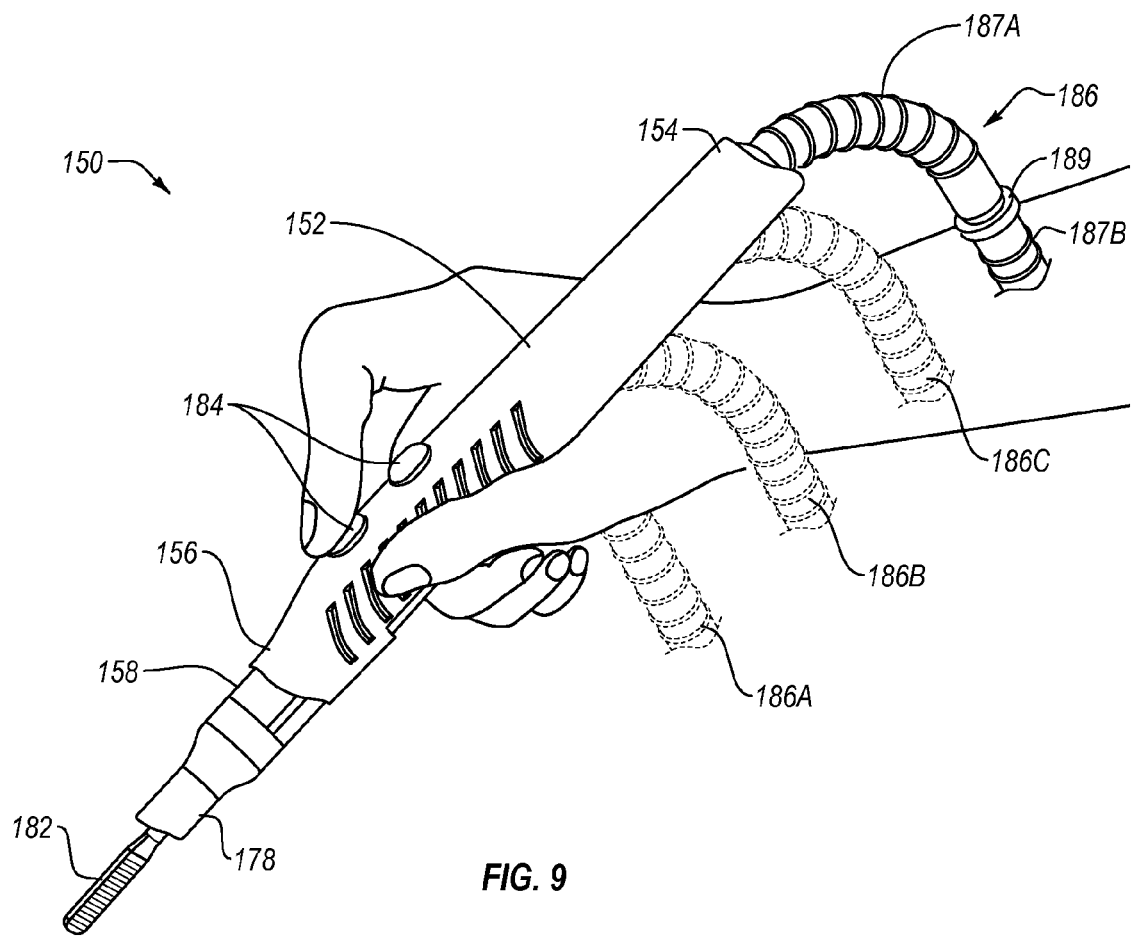
FIG. 9 illustrates the electrosurgical instrument of FIG. 3 being held with the utility conduit exiting the electrosurgical instrument from multiple exemplary exit locations.

FIGS. 6, 7A, 7B, and 9 illustrate utility conduit 186 exiting from various example exit locations along the length of hand piece 152. For instance, utility conduit 186A may exit through slots 170, 192 below input devices 184. As shown in FIG. 9, when utility conduit 186A exits electrosurgical instrument 150 at this location and a user holds electrosurgical instrument 150, utility conduit 186A may be positioned in the palm of the user's hand. As a result, the user may grasp utility conduit 186A by wrapping some or all of his or her fingers around utility conduit 186A. While grasping utility conduit 186A, the user may also hold hand piece 152 as shown in FIG. 9 (e.g., between the thumb and middle finger, with the index finger on top to control input devices 184). In this arrangement, utility conduit 186A may act as a handle for electrosurgical instrument 150. Additionally, utility conduit 186A may be formed to provide stability to electrosurgical instrument 150. For instance, utility conduit 186A may be formed of or include a tubing that is stiff enough to maintain the position or orientation of hand piece 152 when utility conduit 186A is used as a handle. More specifically, utility conduit 186A may be stiff enough so that utility conduit 186A maintains hand piece 152 in its current position even when a physician lets go of hand piece 152 and is only holding utility conduit 186A. Furthermore, utility conduit 186A may be sized to comfortably fit within a user's hand and allow for the user to securely hold utility conduit 186A.

To provide the above noted stability and grip functionalities, a utility conduit may have an outer diameter of between about 0.1 inches and about 3 inches. In one example embodiment, a utility conduit has an outer diameter of about 0.5 inches. A utility conduit may also have some elastic flexibility that contributes to the above-noted functionality. For instance, a utility conduit may be formed to allow for the utility conduit to be angled or bent without collapsing or significantly reducing the inner lumen or flow channel therein. By way of example, the material used to form the utility conduit may allow the utility conduit to have a bend radius of between about 0° and about 180°. In the case of a utility conduit with a bend radius of about 180°, a swivel may be connected between the utility conduit and the hand piece to allow the utility conduit to extend away from the hand piece as shown in the Figures. In other embodiments, all or portions of a utility conduit may be segmented and joined together to provide a moving joint flexibility.

Utility conduit 186 may also exit from other exit locations along the length of hand piece 152. For instance, as shown in FIGS. 6 and 7B, utility conduit 186B is shown exiting hand piece 152 through slot 192. As shown in FIG. 9, this exit location for utility conduit 186B may be near the crook of the user's hand so that utility conduit 186B extends down the crook of the hand towards the wrist. Still further, utility conduit 186C may exit hand piece 152 at a location even closer to proximal end 154, as shown in FIGS. 6, 7A, 7B, and 9.

Slots 170, 192 are configured to allow a user to select substantially any location along the length of hand piece 152 as an exit location. For instance, a user with a larger hand may desire utility conduit 186 to exit closer to proximal end 154. This can be accomplished by simply positioning more of utility conduit 186 within hand piece 152 and extendable shaft 158 so that the exit location of utility conduit 186 is closer to proximal end 154. Alternatively, a user with a smaller hand may desire utility conduit 186 to exit closer to distal end 156. This can be accomplished by positioning a shorter length of utility conduit 186 within hand piece 152. Thus, slots 170, 192 allow a user to customize instrument 150 so that instrument 150 is most comfortable to that user and reduces the resistance and fatigue caused by the weight of utility conduit 186.

As noted herein, a cable or hose that exits from a proximal end of a hand piece creates resistance, typically in the form of a torque, to the movement of the hand piece. Thus, when a user manipulates the hand piece, either to move the hand piece to a new location or to reorient the hand piece within the same general location, the cable or hose resists the movement or reorientation of the hand piece. Accordingly, allowing the exit location of utility conduit 186 to be adjusted along the length of hand piece 152 reduces the amount of resistance typically created by the cable or hose.

In addition to reducing the overall resistance typically created by a cable or hose, moving the exit location of utility conduit 186 closer to the distal end of hand piece 152 also reduces the change is resistance experienced when moving or reorienting hand piece 152. As a hand piece 152 is moved or reoriented, the resistance created by a cable or hose changes. While the change in resistance may be due at least in part to the direction of movement or reorientation and/or the speed of the movement, the change in resistance is primarily due to the exit location of the cable or hose. As discussed herein, the increased distance between the exit location and the pivot point of the hand piece creates a larger torque. As a result, when the exit location of the cable or hose is at or near the proximal end of the hand piece, the change in resistance during movement or reorientation of the hand piece is greater than the change in resistance created when the exit location is closer to the distal end of the hand piece.

With reference to FIG. 9, for instance, when utility conduit 186 extends out of proximal end 154 of hand piece 252, utility conduit 186 creates resistance to the movement of hand piece 152. Additionally, as hand piece 152 is moved or reoriented, the resistance created by utility conduit 186 changes. When utility conduit 186 exits hand piece 152 from a location closer to the distal end 156 of hand piece 152, the resistance created by utility conduit 186 is reduced. Additionally, the change in resistance created by utility conduit 186 when hand piece 152 is moved or reoriented is also reduced as the exit location of utility conduit 186 moves toward the distal end 156 of hand piece 152. When utility conduit 186 exits near the distal end 156 of hand piece 152 (e.g., as illustrated by utility conduit 186A), the resistance and change in resistance created by utility conduit 186 falls dramatically. In such arrangements, the resistance and change in resistance may drop to near zero or at least negligible levels.

The following tables demonstrate that the amount of torque resulting from a distally located exit location is significantly lower than when the exit location is disposed at or near the proximal end of a hand piece. The torque resulting from the cables and/or hoses connected to numerous hand pieces were measured. Specifically, the torques associated with eleven different devices were measured at various heights and at various orientations. Devices 1-4 were standard electrosurgical instruments that include power cables extending from the proximal ends of the hand pieces. Devices 5-10 were electrosurgical instruments that include both power cables and smoke evacuation hoses extending from the proximal ends of the hand pieces. The torque associated with electrosurgical instrument 150 was also measured with utility conduit 186 extending from two different exit locations. The first exit location was at proximal end 154 as shown in FIG. 7A. The second exit location was below user inputs 184 as shown by utility conduit 186A in FIG. 7A.

Table 1 includes the torques associated with the eleven devices when the hand pieces were in a level orientation (i.e., the proximal and distal ends of the hand pieces were at substantially the same height). In contrast, Table 2 includes the torques associated with the eleven devices when the hand pieces were held at a 45° angle with the distal end of the hand piece being disposed lower than the proximal end. In addition to measuring the torques when the devices were at different orientations, the torques were also measured when the hand pieces were held at different heights (i.e., 2.5 ft, 3 ft, 3.5 ft, and 4 ft).

Tables 1 and 2 also include other basic information regarding each of the evaluated devices. This information includes the lengths of the hand pieces, the masses of the hand piece and associated cables/hoses, and the distances between the pivot points of the hand pieces and the ends of the hand pieces. To provide consistency throughout the samples, the pivot point for each hand piece was determined to be at the user input button positioned closest to the proximal end of the hand piece.

TABLE 1

|  | Height above floor | | | | Center of Proximal Input Button to Tip (in.) | Center of Proximal Input Button to exit location (in.) | Total (in.) | Mass of hand piece, cord, & tubing (g) |
| --- | --- | --- | --- | --- | --- | --- | --- | --- |
|  | 2.5 ft | 3.0 ft | 3.5 ft | 4.0 ft | | | | |
|  | Torque (oz. in.) | | | | | | | |
| Electrosurgical Devices | | | | | | | | |
| Device 1 | 1.25 | 1.5 | 1.75 | 2 | 3.82 | 3.82 | 7.64 | 73.24 |
| Device 2 | 2 | 2.5 | 3 | 3.5 | 3.85 | 3.8 | 7.65 | 104.19 |
| Device 3 | 0.65 | 0.9 | 1.2 | 1.5 | 4.1 | 3.82 | 7.92 | 62.69 |
| Device 4 | 0.65 | 0.8 | 1 | 1.25 | 4.2 | 3.3 | 7.50 | 66.3 |
| Smoke Evac Devices | | | | | | | | |
| Electrosurgical Instrument 150 (utility conduit extending from proximal end) | 5 | 5.75 | 6.75 | 7 | 3.83 | 3.83 | 7.66 | 146.81 |
| Electrosurgical Instrument 150 (utility conduit exiting near input button) | 0 | 0 | 0 | 0 | 3.82 | 0.15 | 3.97 | 146.81 |
| Device 5 | 4.5 | 5.5 | 6.5 | 7 | 4.2 | 4 | 8.20 | 216.27 |
| Device 6 | 1.75 | 3 | 4.5 | 7.5 | 3.97 | 3.96 | 7.93 | 268.73 |
| Device 7 | 4.5 | 5.5 | 6.5 | 7.5 | 3.33 | 3.5 | 6.83 | 180.87 |
| Device 8 | 3.75 | 5.75 | 6 | 6.75 | 4.43 | 3.7 | 8.13 | 141.64 |
| Device 9 | 3.25 | 4.5 | 5.25 | 6.25 | 4.24 | 4.24 | 8.48 | 157.88 |
| Device 10 | 1.5 | 1.75 | 2 | 2.25 | 4.12 | 2.57 | 6.69 | 128.73 |

TABLE 2

|  | Height above floor | | | | Center of Proximal Input Button to Tip (in.) | Center of Proximal Input Button to exit location (in.) | Total (in.) | Mass of hand piece, cord, & tubing (g) |
| --- | --- | --- | --- | --- | --- | --- | --- | --- |
|  | 2.5 ft | 3.0 ft | 3.5 ft | 4.0 ft | | | | |
|  | Torque (oz. in.) | | | | | | | |
| Electrosurgical Devices | | | | | | | | |
| Device 1 | 1.5 | 1.75 | 2 | 2.3 | 3.82 | 3.82 | 7.64 | 73.24 |
| Device 2 | 2.25 | 2.75 | 3.25 | 3.5 | 3.85 | 3.8 | 7.65 | 104.19 |
| Device 3 | 0.7 | 1.25 | 1.5 | 1.75 | 4.1 | 3.82 | 7.92 | 62.69 |

TABLE 2-continued

| | Height above floor | | | | Center of Proximal Input Button to Tip (in.) | Center of Proximal Input Button to exit location (in.) | Total (in.) | Mass of hand piece, cord, & tubing (g) |
|---|---|---|---|---|---|---|---|---|
| | 2.5 ft | 3.0 ft | 3.5 ft | 4.0 ft | | | | |
| | Torque (oz. in.) | | | | | | | |
| Device 4 | 1 | 1.25 | 1.5 | 1.75 | 4.2 | 3.3 | 7.50 | 66.3 |
| Smoke Evac Devices | | | | | | | | |
| Electrosurgical Instrument 150 (utility conduit extending from proximal end) | 5 | 5.75 | 6.75 | 7 | 3.83 | 3.83 | 7.66 | 146.81 |
| Electrosurgical Instrument 150 (utility conduit exiting near input button) | 0 | 0 | 0 | 0 | 3.82 | 0.15 | 3.97 | 146.81 |
| Device 5 | 4.5 | 5.5 | 6.5 | 7 | 4.2 | 4 | 8.20 | 216.27 |
| Device 6 | 1.75 | 3 | 4.5 | 7.5 | 3.97 | 3.96 | 7.93 | 268.73 |
| Device 7 | 4.5 | 5.5 | 6.5 | 7.5 | 3.33 | 3.5 | 6.83 | 180.87 |
| Device 8 | 3.75 | 5.75 | 6 | 6.75 | 4.43 | 3.7 | 8.13 | 141.64 |
| Device 9 | 3.25 | 4.5 | 5.25 | 6.25 | 4.24 | 4.24 | 8.48 | 157.88 |
| Device 10 | 1.5 | 1.75 | 2 | 2.25 | 4.12 | 2.57 | 6.69 | 128.73 |

As can be seen from the data in Tables 1 and 2, the power cables for the standard electrosurgical devices create torques ranging from 0.65 oz. in. to 3.5 oz. in. in the horizontal orientation and from 0.7 oz. in. to 3.5 oz. in. in the angled orientation. Similarly, the power cables and hoses for Devices 5-10 create torques ranging from 1.5 oz. in. to 7.5 oz. in. in both the horizontal and angled orientations. It is observed that the torque for each device generally increases as the height of the hand piece increases. This is understandable since the length, and thus the weight, of the suspended portion of the power cable and/or evacuation hose increases as the height of the hand piece increases.

With regard to electrosurgical instrument 150, it is noted that the torque from utility conduit 186 is significantly higher when utility conduit exits hand piece 152 at proximal end 154 than when utility conduit 186 exits hand piece 152 near user inputs 184. Specifically, when utility conduit exits hand piece 152 at proximal end 154, utility conduit 186 creates torques ranging from 5 oz. in. to 7 oz. in., depending on the height of hand piece 152. In contrast, when utility conduit 186 exits hand piece 152 near user inputs 184, utility conduit 186 creates no torque, or negligible levels of torque. Thus, by allowing the exit location of utility conduit 186 to be adjusted along the length of hand piece 152, a user can customize electrosurgical instrument 150 to provide torques ranging anywhere from about 0 oz. in. up to about 7 oz. in. or more.

As can be seen in FIGS. 7A and 7B, depending on the position of extendable shaft 158 relative to hand piece 152 and the exit location of utility conduit 168, utility conduit 168 may pass through one or both of slots 170, 192. By way of example, when extendable shaft 158 is in the fully retracted position shown in FIG. 7A, utility conduit 186 may pass through both of slots 170, 192 when exiting hand piece 152. In contrast, when extendable shaft 158 is in the fully extended position shown in FIG. 7B, utility conduit 186 may only pass through slot 192 when exiting hand piece 152. For instance, utility conduits 186B, 186C are shown in FIG. 7B passing through slot 192, but not through slot 170. Nevertheless, even when extendable shaft 158 is in the fully extended position, utility conduit 186 may still pass through both of slots 170, 192, as illustrated in FIG. 7B with utility conduit 186A passing through both of slots 170, 192.

Additionally, utility conduit 186 may pass through different portions of slots 170, 192. The portions of slots 170, 192 through which utility conduit 186 passes may or may not correspond to one another. For instance, when extendable shaft 158 is in the fully retracted position shown in FIG. 7A, utility conduit 186 may pass through corresponding portions of slots 170, 192 when exiting hand piece 152. More specifically, as shown in FIG. 7A, utility conduit 186A passes through the distal ends of slots 170, 192. Similarly, utility conduit 186B passes through intermediate portions of slots 170, 192 and utility conduit 186C passes through the proximal ends of slots 170, 192.

In contrast, when extendable shaft 158 is in the fully extended position shown in FIG. 7B, utility conduit 186 may pass through non-corresponding portions of slots 170, 192 when exiting hand piece 152. For instance, as shown in FIG. 7B, utility conduit 186A passes through the proximal end of slot 170 and the distal end of slot 192. In other instances, such as when extendable shaft 158 is in one of the one or more intermediate positions, utility conduit 186 may pass through a proximal end of slot 170 and an intermediate portion of slot 192. Likewise, utility conduit 186 may pass through an intermediate portion of slot 170 and the distal end of slot 192.

Notably, by connecting utility conduit 186 adjacent distal end 162 of extendable shaft 158, hand piece 152 and extendable shaft 158 do not include or act as a smoke/fluid conveying conduit. For instance, hand piece 152 does not have to include a closed channel or other conduit that extends from distal end 156 to proximal end 154 and that is sealed along its entire length. Similarly, extendable shaft 158 does not have to include a closed channel or other conduit that extends from distal end 162 to proximal end 160 and that is sealed along its entire length. Furthermore, the interface between hand piece 152 and extendable shaft 158 does not have to be sealed.

With a typical smoke evacuation device, a first seal is required between the nozzle and a distal end of a conduit in the hand piece and a second seal is required between a proximal end of the conduit in the hand piece and the smoke evacuation hose. Furthermore, when an extendable tube is included, the interface between the extendable tube and the conduit in the hand piece has to be sealed. Because utility conduit 186 is connected and sealed adjacent to nozzle 178, a second seal is not required between extendable shaft 158 and hand piece 152 or between proximal end 154 and utility conduit 186.

Connecting utility conduit 186 near distal end 162 also provides a flow channel that has a generally uniform diameter from distal end 162 to an associated vacuum device. More specifically, the interior of utility conduit 186 provides a flow channel through which smoke/fluids may be conveyed away from a surgical site. Because utility conduit 186 has a generally uniform inner diameter throughout its length, the flow channel from distal end 162 of extendable shaft 158 to an associated vacuum device is generally uniform. As will be appreciated by one of ordinary skill in the art, a generally uniform flow channel provides increased flow efficiency of the smoke/fluid being conveyed away. In contrast, common smoke evacuation devices include a flow channel through a hand piece and a smoke evacuation hose that have different diameters, thereby reducing the flow efficiency therethrough.

Slots 170, 192 may be generally straight and smooth to allow for utility conduit 186 to exit hand piece 152 and extendable shaft 158 at substantially any location along the length of hand piece 152. Accordingly, slots 170, 192 may allow for the exit location of utility conduit 186 to be continuously variable. In other words, the exit location of utility conduit 186 may be selectively adjusted to substantially any location along the length of hand piece 152.

As can be seen in FIG. 6, slots 170, 192 may also include one or more cutouts that allow utility conduit 186 to exit hand piece 152 at one or more predefined, discrete exit locations along the length of hand piece 152. For instance, slot 192 includes a cutout 196 just proximal to retainer portion 194. Similarly, slot 170 includes multiple cutouts 198 at various positions along the length thereof which can be aligned with cutout 196 (e.g., when extendable shaft 158 is extended or retracted). Cutouts 196, 198 are wider than the rest of slots 170, 192 to allow utility conduit 186 to exit hand piece 152 and extendable shaft 158 therethrough. Slot 192 may also include one or more additional cutouts at various positions along the length thereof to provide multiple discrete exit locations along the length of hand piece 152.

As can be seen in the Figures, at least a portion of utility conduit 186 may be corrugated, convoluted, fluted, or have detents disposed on the outer surface thereof. The corrugation, flutes, or detents on utility conduit 186 may facilitate secure holding of utility conduit 186 within slots 170, 190 and/or create one or more predefined, discrete exit locations along the length of hand piece 152. More specifically, the exit locations may be defined by the corrugations, convolutions, flutes, or detents on utility conduit 186. It will be understood, however, that utility conduit 186 may not be corrugated, convoluted, fluted, or include detents thereon. Additionally, it is understood that any combination of a utility conduit (corrugated, convoluted, fluted, detented, or smooth) and slots (straight or with cutouts) may be used.

As noted, a utility conduit may be formed from multiple sections. The sections of the utility conduit may have diameters and/or flexibility characteristics that are difference from one another. For instance, a first section connected to the hand piece may be relatively stiff to provide the above-noted stability and grip functionalities. In contrast, a second section connected to the first section may be more flexible than the first section.

As also noted herein, a utility conduit may be formed by one or more cables and/or one or more hoses. Accordingly, the noted diameters and flexibilities may be a result of multiple hoses, cables, and/or combinations thereof. For instance, two or more hoses may have a combined diameter of between about 0.1 inches and about 3 inches.

Figure 10:
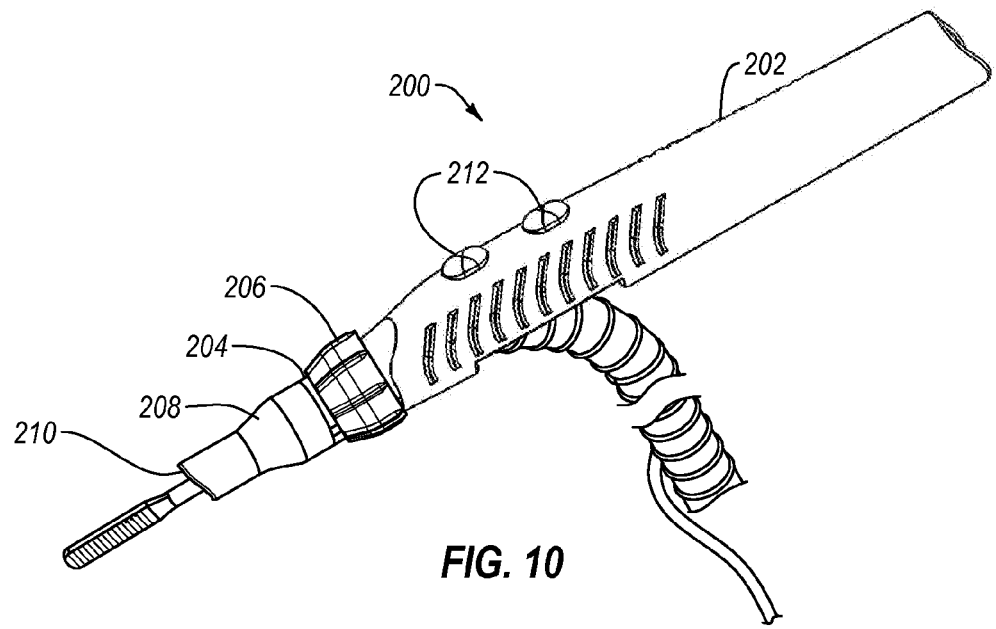
FIG. 10 is a perspective view of an electrosurgical instrument according to another exemplary embodiment of the present invention.
Figure 11:
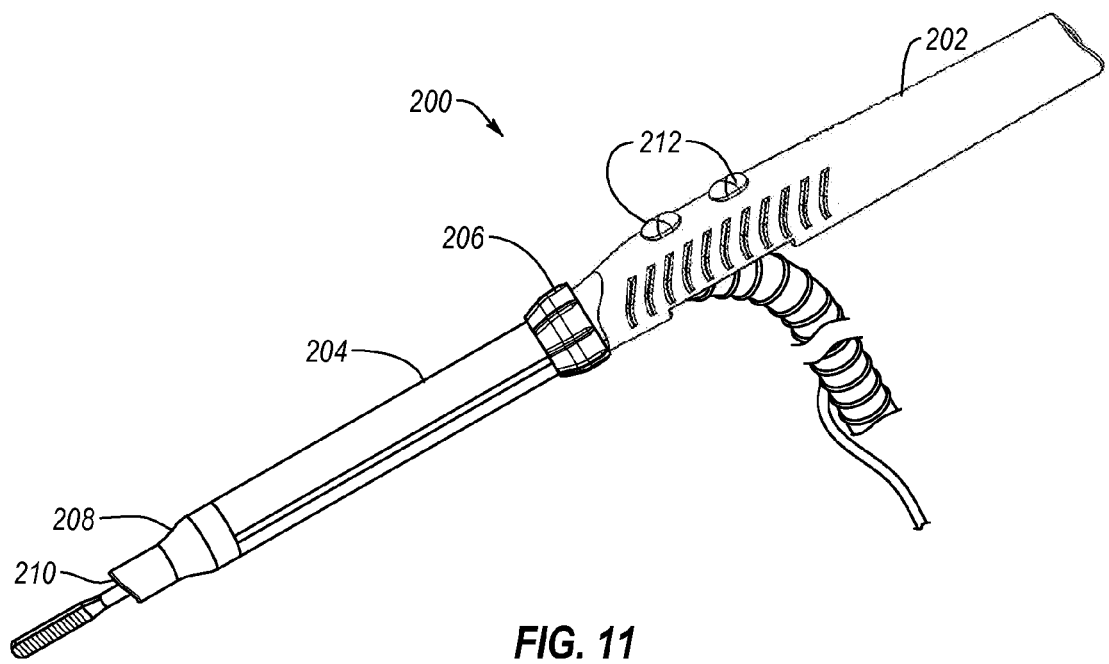
FIG. 11 is another perspective view of the electrosurgical instrument of FIG. 10 in an extended configuration.
Figure 12:
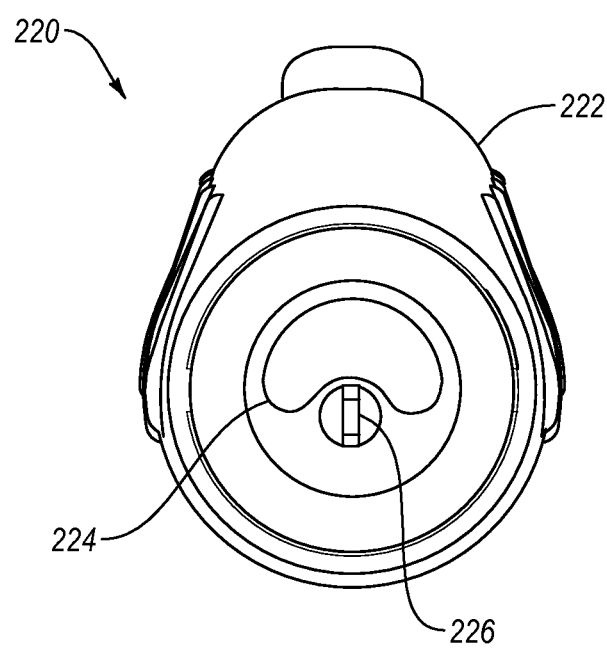
FIG. 12 is an end view of a distal end of an electrosurgical instrument according to another exemplary embodiment of the present invention.

Attention is now directed to FIGS. 10-12, which illustrate electrosurgical instruments similar to electrosurgical instrument 150, but that include additional or alternative features. Accordingly, particularly attention will be directed to the additional or alternative features, with the understanding that these features may replace or be combined with the other features described herein.

FIGS. 10-11 illustrate an electrosurgical instrument 200 that includes a hand piece 202 and an extendable shaft 204 that is selectively extendable relative to hand piece 202. In contrast to extendable shaft 158, which is selectively securable in a plurality of discrete positions, extendable shaft 204 is securable in an infinite number of positions relative to hand piece 202. More specifically, extendable shaft 204 may be secured relative to hand piece 202 in a fully retracted position (FIG. 10), a fully extended position (FIG. 11), and an infinite number of positions therebetween. That is, a user may position extendable shaft 204 at any position at or between the fully retracted and fully extended positions and extendable shaft 204 can be secured in the selected position.

A locking nut 206 may be used to secure extendable shaft 204 in the desired position relative to hand piece 202. As can be seen, locking nut 206 is disposed around extendable shaft 204. Locking nut 206 can be selectively screwed or otherwise attached onto the distal end of hand piece 202. When locking nut 206 is screwed or otherwise attached onto hand piece 202, the radius of an internal bore in locking nut 206 decreases. The decreased radius of the bore in locking nut 206 increases the friction between locking nut 206 and extendable shaft 202, thereby securing extendable shaft 202 in the desired position.

Electrosurgical instrument 200 also includes a nozzle 208 disposed at the end of extendable shaft 204. Disposed on the end of nozzle 208 is a light 210. Light 210 may be used during an electrosurgical procedure to illuminate the surgical site. Light 210 may be activated by input devices 212.

FIG. 12 illustrates a view of the distal end of an electrosurgical instrument 220. As can be seen, electrosurgical instrument 220 includes a hand piece 222 with a nozzle 224 into which smoke/fluid can be drawn. Electrosurgical instrument 220 also includes an electrode tip 226 mounted in the distal end thereof. Unlike electrode tip 182 that is disposed within the flow channel of nozzle 178, electrode tip 226 is mounted outside of the flow channel of nozzle 224. As a result, electrode tip 226 does not obstruct the flow channel of nozzle 224 at all.

For various reasons it can be beneficial to have electrode tip 226 generally aligned with a longitudinal axis of electrosurgical instrument 220. For instance, when a user rotates electrosurgical instrument 220 about the longitudinal axis, electrode tip 226 will rotate, but not revolve, around the axis. As a result, the orientation of electrode tip 226 may change, but not the location.

In order to allow for electrode tip 226 to be aligned with the axis of electrosurgical instrument 220 and to provide a large enough flow channel through nozzle 224, the opening in nozzle 224 may wrap at least partially around electrode tip 226. For instance, as seen in FIG. 12, the opening in nozzle 224 can be generally kidney shaped, with the ends of the opening extending at least partially around electrode tip 226. It is understood, that the opening in nozzle 224 may take other shapes without departing from the scope of the invention.

While the embodiments disclosed herein have been directed to electrosurgical instruments with adjustable utility conduits and extendable shafts, the present invention is not intended to be limited only to electrosurgical instruments. Rather, the present invention is broadly directed to any hand-held instrument that includes one or more of the features described herein. Examples of such hand-held instruments may include, but are not limited to, dental instruments (e.g., drills, polishing tools, scalers, compressed air tools, suction tools, irrigation tools, carries detection tools, water flossing tool (e.g., waterpik)), soldering tools (e.g., heated tools, smoke collection tools, de-soldering tools), high speed grinding and polishing tools (e.g., Dremel tools, carving tools, manicure tools, dental lab grinders/polishers), laser treatment instruments, laser surgical instruments, light probes, suction handles (e.g., Yankauser), blasting tools (e.g., sandblast, gritblast), shockwave therapy tools, ultrasonic therapy tools, ultrasonic probe tools, ultrasonic surgical tools, adhesive application instruments, glue guns, pneumatic pipettes, welding tools, RF wrinkle therapy hand pieces, phaco hand pieces, shears, shaver, or razor hand pieces, micro drill hand pieces, vacuum hand pieces, small parts handling hand pieces, tattoo needle handles, small torch hand pieces, electrology hand pieces, low speed grinding, polishing and carving tools, permanent makeup hand pieces, electrical probe hand pieces, ferromagnetic surgical hand pieces, surgical suction instruments (e.g., liposuction cannulas), surgical suction cannulas, microdermabrasion hand pieces, fiberoptic camera handles, microcamera hand pieces, pH probe hand pieces, fiberoptic and LED light source hand pieces, hydrosurgery hand pieces, orthopedic shaver, cutter, burr hand pieces, wood burning tools, electric screwdrivers, electronic pad styluses, and the like.

Furthermore, the present invention is not limited to hand-held instruments that allow for the adjustment of an exit location of a utility conduit therefrom. Rather, the present invention also encompasses hand-held instruments that have a utility conduit connected thereto and that extend therefrom at a location other than at the proximal end of the hand-held instrument. For instance, the exit location of the utility conduit may not be adjustable along the length of the hand-held instrument. Nevertheless, the exit location of the utility conduit may be positioned at a location along the length of the hand-held instrument that is away from the proximal end of the hand-held instrument.

Even more specifically, the hand-held instrument may have a central portion disposed approximately midway between the proximal and distal ends of the instrument. The exit location of the utility conduit may be positioned at about the central portion of the hand-held instrument or between the central portion and the distal end of the hand-held instrument. The hand-held instrument may also have a three-quarter portion disposed approximately midway between the central portion and the proximal end. In other words, approximately one quarter of the length of the hand-held instrument is disposed between the proximal end and the three-quarter portion, while three quarters of the length of the hand-held instrument are disposed between the three-quarter portion and the distal end. The exit location of the utility conduit may be positioned at about the three-quarter portion of the hand-held instrument or between the three-quarter portion and the distal end of the hand-held instrument.

Still further, the present invention is not limited to hand-held instruments that have extendable shafts for increasing the reach of operational capabilities of the instrument. Rather, instruments according to the present invention may include electrode tips and/or smoke/fluid capture features that are fixed relative to a hand piece. Likewise, instruments according to the present invention may provide electrosurgical capabilities, but not smoke/fluid capture capabilities. In contrast, instruments according to the present invention may provide smoke/fluid capture capabilities, but not electrosurgical capabilities.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A hand-held instrument comprising:
a hand piece configured to be held by a user, the hand piece having a proximal end and a distal end;
an extendable shaft movably associated with and disposed at least partially within the hand piece, the extendable shaft having a proximal end and a distal end and being selectively movable relative to the hand piece between a retracted position and an extended position, the proximal end of the extendable shaft being movably disposed within the hand piece such that the proximal end of the extendable shaft is positioned closer to the distal end of the hand piece when the extendable shaft is in the extended position than when the extendable shaft is in the retracted position;
a nozzle disposed at the distal end of the extendable shaft, the nozzle being adapted to have smoke, gas, or fluid drawn therethrough; and
a utility conduit connected to the distal end of the extendable shaft, the utility conduit comprising a power cable for transmitting electrical energy to the hand piece and an evacuation hose in fluid communication with the nozzle, the evacuation hose being configured to convey away the smoke, gas, or fluid drawn into the nozzle, wherein the utility conduit moves with the extendable shaft and relative to the hand piece when the extendable shaft moves between the retracted position and the extended position.

2. The hand-held instrument of claim 1, wherein, when the extendable shaft is in the retracted position, the connection between the utility conduit and the distal end of the extendable shaft is disposed at a first position relative to the distal end of the hand piece, and wherein, when the extendable shaft is in the extended position, the connection between the utility conduit and the distal end of the extendable shaft is disposed at a second position relative to the distal end of the hand piece, the second position being located more distal relative to the distal end of the hand piece than the first position.

3. The hand-held instrument of claim 1, wherein the utility conduit is configured to exit the hand piece at an exit location disposed between the proximal end and distal end of the hand piece.

4. The hand-held instrument of claim 3, wherein the exit location of the utility conduit is selectively adjustable between the proximal end and distal end of the hand piece.

5. The hand-held instrument of claim 4, wherein the utility conduit creates a torque on the hand piece, and wherein the torque decreases from a maximum level when the utility conduit exits the hand piece adjacent to the proximal end to a minimum level when the utility conduit exits the hand piece at about the midway point between the proximal and distal ends of the hand piece.

6. The hand-held instrument of claim 1, wherein the extendable shaft is securable in the retracted position, the extended position, and one or more intermediate positions.

7. The hand-held instrument of claim 6, wherein the extendable shaft comprises a plurality of recesses and the hand piece comprises one or more protrusions, wherein the plurality of recesses and the one or more protrusions cooperate to secure the extendable shaft in the retracted position, the extended position, and the one or more intermediate positions, wherein the plurality of recesses are disposed in the extendable shaft such that the plurality of recesses move with the extendable shaft and relative to the one or more protrusions.

8. The hand-held instrument of claim 1, wherein the hand piece comprises a slot extending from the proximal end toward the distal end thereof, wherein the slot enables the utility conduit to pass therethrough to exit the hand piece.

9. The hand-held instrument of claim 8, wherein the extendable shaft comprises a slot extending from the proximal end toward the distal end of the extendable shaft, wherein the slot in the extendable shaft enables the utility conduit to pass therethrough to exit the extendable shaft between the proximal end and the distal end of the extendable shaft.

10. The hand-held instrument of claim 9, wherein the slot in the hand piece and the slot in the extendable shaft each comprise one or more cutouts that may be selectively aligned with one another to define one or more discrete exit locations between the proximal end and distal end of the hand piece.

11. A hand-held instrument comprising:
a hand piece having a proximal end, a distal end, and a slot extending from the proximal end toward the distal end;
an extendable shaft that is selectively movable relative to the hand piece between a fully retracted position and a fully extended position, the extendable shaft having a proximal end, a distal end, and a slot extending from the proximal end toward the distal end, the slot in the extendable shaft being generally aligned with the slot in the hand piece when the extendable shaft is in the fully retracted position;
a nozzle disposed at the distal end of the extendable shaft, the nozzle being adapted to have smoke, gas, or fluid drawn therethrough; and
a utility conduit connected to the distal end of the extendable shaft, the utility conduit comprising a power cable for transmitting electrical energy to the hand piece and an evacuation hose in fluid communication with the nozzle, the evacuation hose being configured to convey away the smoke, gas, or fluid drawn into the nozzle, the utility conduit being configured to move with the extendable shaft and relative to the hand piece when the extendable shaft is moved between the fully retracted position and the fully extended position, wherein, when the extendable shaft is in the retracted position, the connection between the utility conduit and the distal end of the extendable shaft is disposed at a first position relative to the distal end of the hand piece, and wherein, when the extendable shaft is in the extended position, the connection between the utility conduit and the distal end of the extendable shaft is disposed at a second position relative to the distal end of the hand piece, the second position being located more distal relative to the distal end of the hand piece than the first position, wherein the alignment of the slot in the extendable shaft and the slot in the hand piece enables the utility conduit to pass through the slot in the extendable shaft and the slot in the hand piece to exit the hand piece at an exit location between the proximal end and the distal end of the hand piece.

12. The hand-held instrument of claim 11, wherein the utility conduit is configured to exit the hand piece at an exit location between the proximal end and the distal end of the hand piece.

13. The hand-held instrument of claim 12, wherein the exit location of the utility conduit is selectively adjustable along a length of the hand piece between the proximal end and the distal end of the hand piece.

14. The hand-held instrument of claim 13, wherein:
the utility conduit creates a torque on the hand piece; and
the torque decreases from a maximum level when the utility conduit exits the hand piece adjacent to the proximal end to a minimum level when the utility conduit exits the hand piece at about the midway point between the proximal and distal ends of the hand piece.

15. The hand-held instrument of claim 14, wherein the maximum level of torque is between about 5 oz. in. and about 7 oz. in. and the minimum level of torque is about 0 oz. in.

16. The hand-held instrument of claim 11, wherein the utility conduit is configured to pass through only the slot in the hand piece to exit the hand piece at an exit location between the proximal end and the distal end of the hand piece when the extendable shaft is in the fully extended position.

17. The hand-held instrument of claim 11, wherein the extendable shaft is selectively movable relative to the hand piece to one or more intermediate positions between the fully retracted position and the fully extended position.

18. The hand-held instrument of claim 11, wherein the hand-held instrument is selected from the group consisting of a medical instrument, a dental instrument, a soldering tool, a wood burning tool, a drill, and an adhesive applicator.

19. A hand-held instrument comprising:
a hand piece configured to be held by a user, the hand piece having a proximal end, a distal end, and a slot extending from the proximal end toward the distal end;
an extendable shaft movably received at least partially within the hand piece, the extendable shaft being selectively movable relative to the hand piece between a retracted position and an extended position, the extendable shaft having a proximal end, a distal end, and a slot extending from the proximal end toward the distal end, the proximal end of the extendable shaft being movably disposed within the hand piece such that the proximal end of the extendable shaft is positioned closer to the distal end of the hand piece when the extendable shaft is in the extended position than when the extendable shaft is in the retracted position;
a nozzle disposed at the distal end of the extendable shaft, the nozzle having an opening therein through which smoke or fluid may be drawn, wherein the nozzle moves with the extendable shaft when the extendable shaft moves between the retracted position and the extended position; and
a utility conduit connected to the distal end of the extendable shaft, the utility conduit comprising a power cable for transmitting electrical energy to the hand piece and an evacuation hose in fluid communication with the nozzle, the evacuation hose being configured to convey away the smoke or fluid drawn into the nozzle, wherein the utility conduit moves with the extendable shaft and relative to the hand piece when the extendable shaft moves between the retracted position and the extended position, wherein:

when the extendable shaft is in the retracted position, the connection between the utility conduit and the distal end of the extendable shaft is disposed at a first position relative to the distal end of the hand piece, when the extendable shaft is in the extended position, the connection between the utility conduit and the distal end of the extendable shaft is disposed at a second position relative to the distal end of the hand piece, the second position being located more distal relative to the distal end of the hand piece than the first position, when the extendable shaft is in the extended position, the utility conduit is configured pass through the slot in the hand piece to exit the hand piece at an exit location between the proximal end and the distal end of the hand piece, and when the extendable shaft is in the retracted position, the utility conduit is configured pass through both the slot in the extendable shaft and the slot in the hand piece to exit the hand piece at an exit location between the proximal end and the distal end of the hand piece.

20. The hand-held instrument of claim 19, wherein the extendable shaft comprises a track in an outer surface thereof and the hand piece comprises a rail disposed on an interior surface thereof, wherein the track and the rail cooperate to substantially prevent relative rotational movement between the extendable shaft and the hand piece.

21. The hand-held instrument of claim 19, further comprising a light disposed adjacent the end of the extendable shaft.

22. The hand-held instrument of claim 19, wherein the hand piece comprises one or more input devices configured to selectively control an operation of the hand-held instrument.

23. The hand-held instrument of claim 22, further comprising an electrical ribbon, the electrical ribbon having a first end connected the one or more input devices and a second end connected to the distal end of the extendable shaft.

24. The hand-held instrument of claim 23, wherein the electrical ribbon is folded over itself such that a first portion of the electrical ribbon extends proximally from the one or more input devices toward the proximal end of the hand piece, and a second portion of the electrical ribbon extends distally towards the distal end of the extendable shaft and inside the extendable shaft.

* * * * *